United States Patent
Levesque et al.

(10) Patent No.: US 6,610,075 B1
(45) Date of Patent: Aug. 26, 2003

(54) KERATOME WITH SUSPENDED STABILIZED BLADE, IMPROVED SUCTION RING WITH APPLANATOR AND GUIDED ENGAGEMENT WITH KERATOME CUTTER HEAD, AUTOMATED TRANSLATION OF THE CUTTER HEAD, AND BLADE INSERTION TOOL

(75) Inventors: Gaston J. Levesque, Meriden, CT (US); David F. Sutton, Milford, CT (US)

(73) Assignee: Becton, Dickenson and Company, Franklin Lakes, NJ (US)

( * ) Notice: Subject to any disclaimer, the term of this patent is extended or adjusted under 35 U.S.C. 154(b) by 0 days.

(21) Appl. No.: 09/434,838

(22) Filed: Nov. 4, 1999

Related U.S. Application Data

(63) Continuation-in-part of application No. 09/178,282, filed on Oct. 23, 1998, now abandoned.
(60) Provisional application No. 60/107,187, filed on Nov. 5, 1998, and provisional application No. 60/063,083, filed on Oct. 24, 1997.

(51) Int. Cl.$^7$ .................................................. A61F 9/00
(52) U.S. Cl. ........................ 606/166; 606/167; 606/107
(58) Field of Search ................................ 606/166, 167, 606/131, 107; 30/32, 37, 38, 42, 43.3, 43.7, 43.8, 43.9, 44, 51, 62, 329–340; 604/19, 22

(56) References Cited

U.S. PATENT DOCUMENTS

| | | |
|---|---|---|
| 5,133,726 A | 7/1992 | Ruiz et al. |
| 5,215,104 A | 6/1993 | Steinert |
| 5,288,292 A | 2/1994 | Giraud et al. |
| 5,318,046 A | 6/1994 | Rozakis |
| 5,336,235 A | 8/1994 | Myers |

(List continued on next page.)

FOREIGN PATENT DOCUMENTS

| | | |
|---|---|---|
| EP | 956 840 A2 | 11/1999 |
| JP | 11-276513 | 11/1999 |
| JP | 11-342151 | 12/1999 |
| WO | WO 00/09055 | 2/2000 |

*Primary Examiner*—Glenn K. Dawson
(74) *Attorney, Agent, or Firm*—James R. Frederick; Ware, Fressola, Van Der Sluys & Adolphson LLP

(57) ABSTRACT

A keratome includes a cutting instrument having a cutter head with a reciprocating blade and a cutting edge extending below a sole surface of the cutter head; an automated drive unit mounting the cutting instrument for powered translational movement of at least the cutter head thereof, and a suction ring including an eye ring adapted to be secured to an eye by suction and defining a cornea aperture for presenting the outer layer of the cornea of the eye for cutting. The suction ring has a shoe from which the eye ring extends, the shoe defining a cutting guideway configured for receiving the cutter head in precision mating sliding engagement when the cutting edge of the blade is positioned over the cornea aperture of the eye ring, and an entrance guideway extending from and generally aligned with the cutting guideway, the entrance guideway configured for receiving the cutter head in orienting sliding engagement and positively positioning the cutter head for precision mating sliding engagement with the cutting guideway. The automated drive unit and the suction ring are configured for releasable attachment when said cutter head is received in the entrance guideway of the suction ring. The automated drive unit is operable to slidingly translate the cutter head into the cutting guideway and to withdraw the cutter head therefrom.

13 Claims, 37 Drawing Sheets

U.S. PATENT DOCUMENTS

| | | |
|---|---|---|
| 5,342,378 A | 8/1994 | Giraud et al. |
| 5,370,652 A | 12/1994 | Kellan |
| 5,395,385 A | 3/1995 | Kilmer et al. |
| 5,496,339 A | 3/1996 | Koepnick |
| 5,527,328 A | 6/1996 | Pintucci |
| RE35,421 E | 1/1997 | Ruiz et al. |
| 5,591,174 A | 1/1997 | Clark et al. |
| 5,595,570 A | 1/1997 | Smith |
| 5,624,456 A | 4/1997 | Hellenkamp |
| 5,658,303 A | 8/1997 | Koepnick |
| 5,690,657 A | 11/1997 | Koepnick |
| 5,772,675 A | 6/1998 | Hellenkamp |
| 5,779,723 A | 7/1998 | Schwind |
| 5,807,380 A | 9/1998 | Dishler |
| 5,817,115 A | 10/1998 | Nigam |
| 5,951,579 A | 9/1999 | Dykes |
| 5,989,272 A | 11/1999 | Barron et al. |
| 5,997,559 A | 12/1999 | Ziemer |
| 6,030,398 A | 2/2000 | Klopotek |
| 6,033,075 A | 3/2000 | Fujieda et al. |
| 6,045,562 A | 4/2000 | Amano et al. |
| 6,059,805 A | 5/2000 | Sugimura et al. |
| 6,071,293 A | 6/2000 | Krumeich |
| 6,083,236 A | 7/2000 | Feingold |
| 6,099,541 A | 8/2000 | Klopotek |
| 6,126,668 A | 10/2000 | Bair et al. |
| 6,203,555 B1 * | 3/2001 | Amano et al. ............... 606/166 |
| 6,228,099 B1 * | 5/2001 | Dybbs ......................... 606/166 |

* cited by examiner

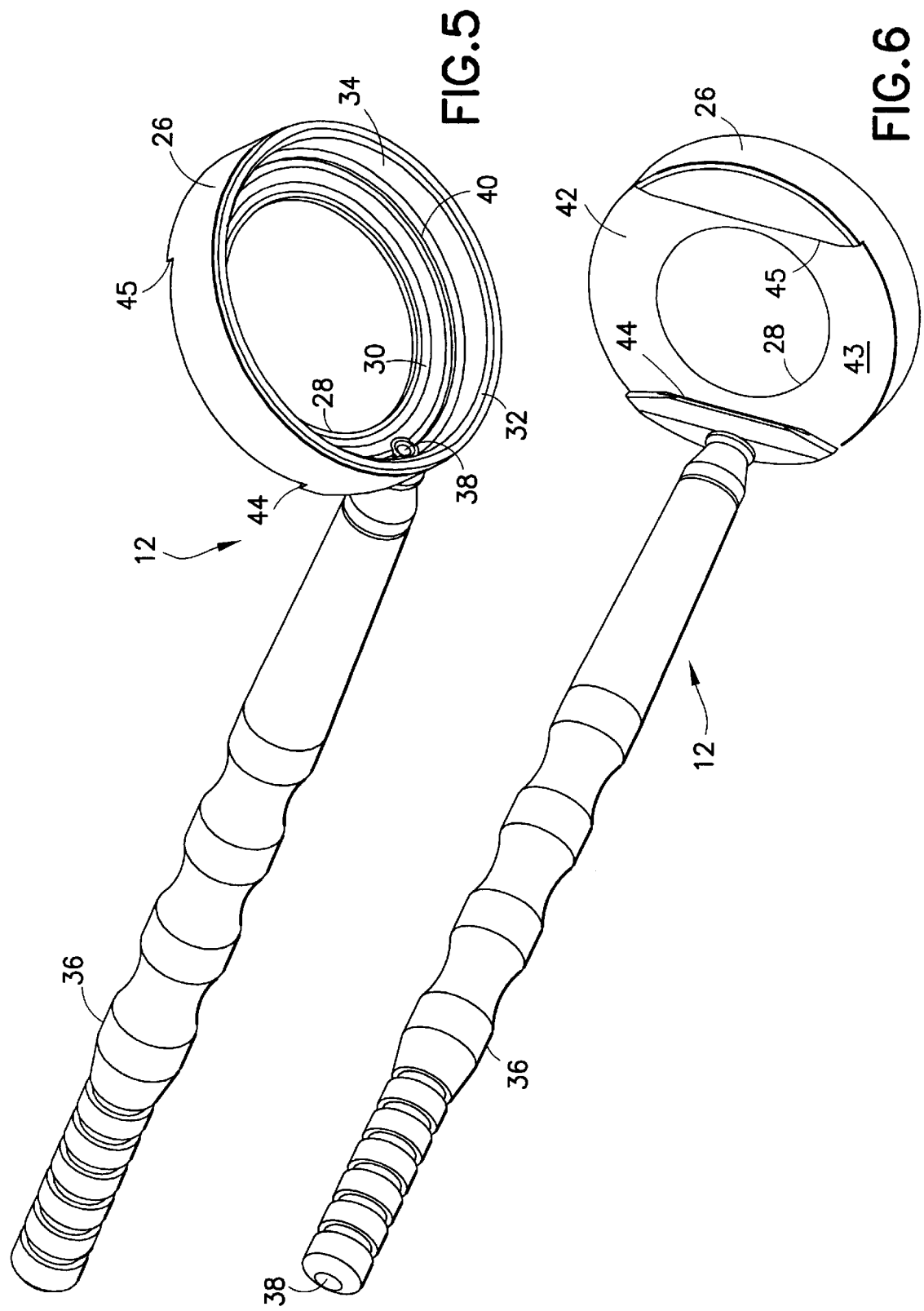

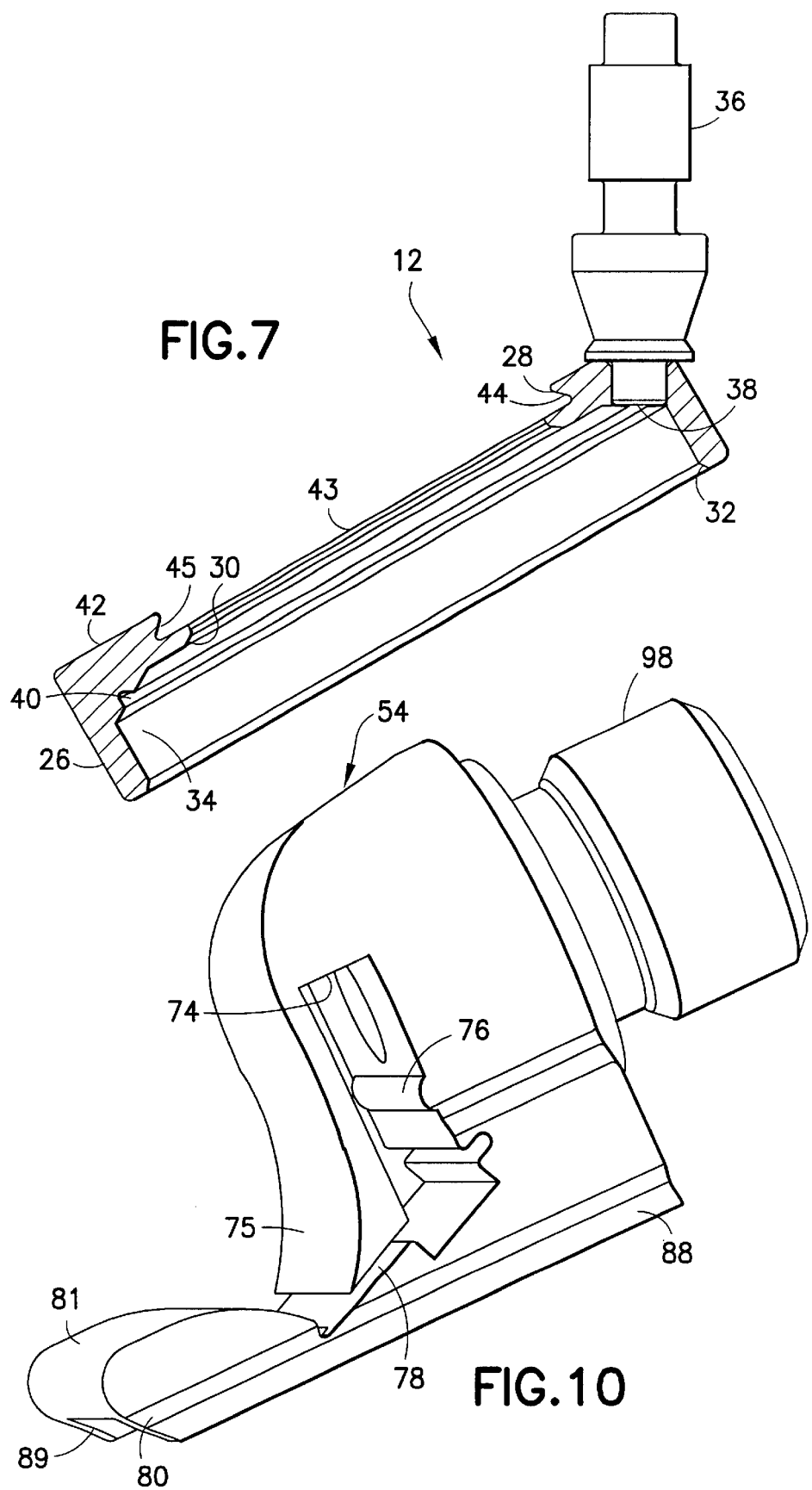

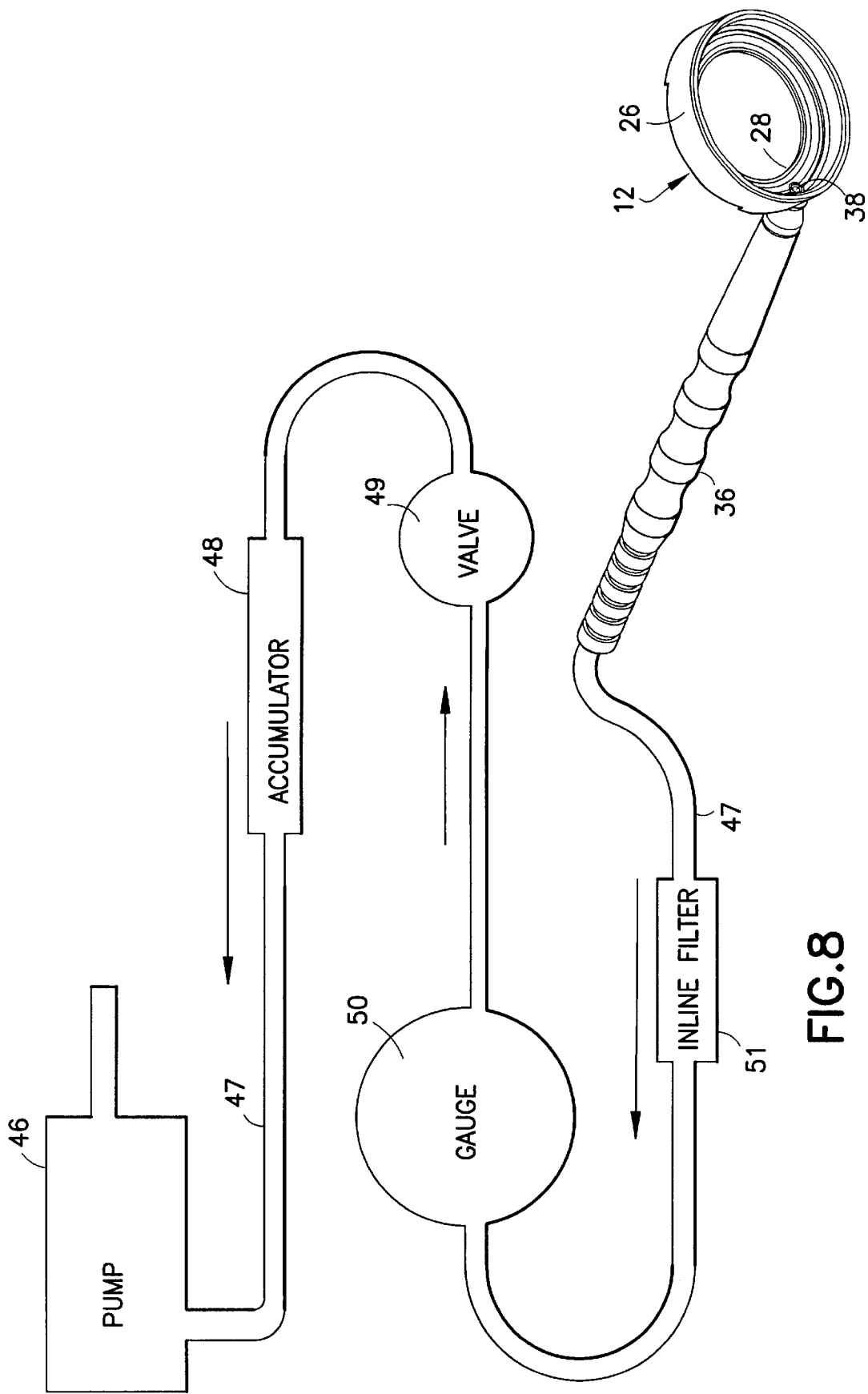

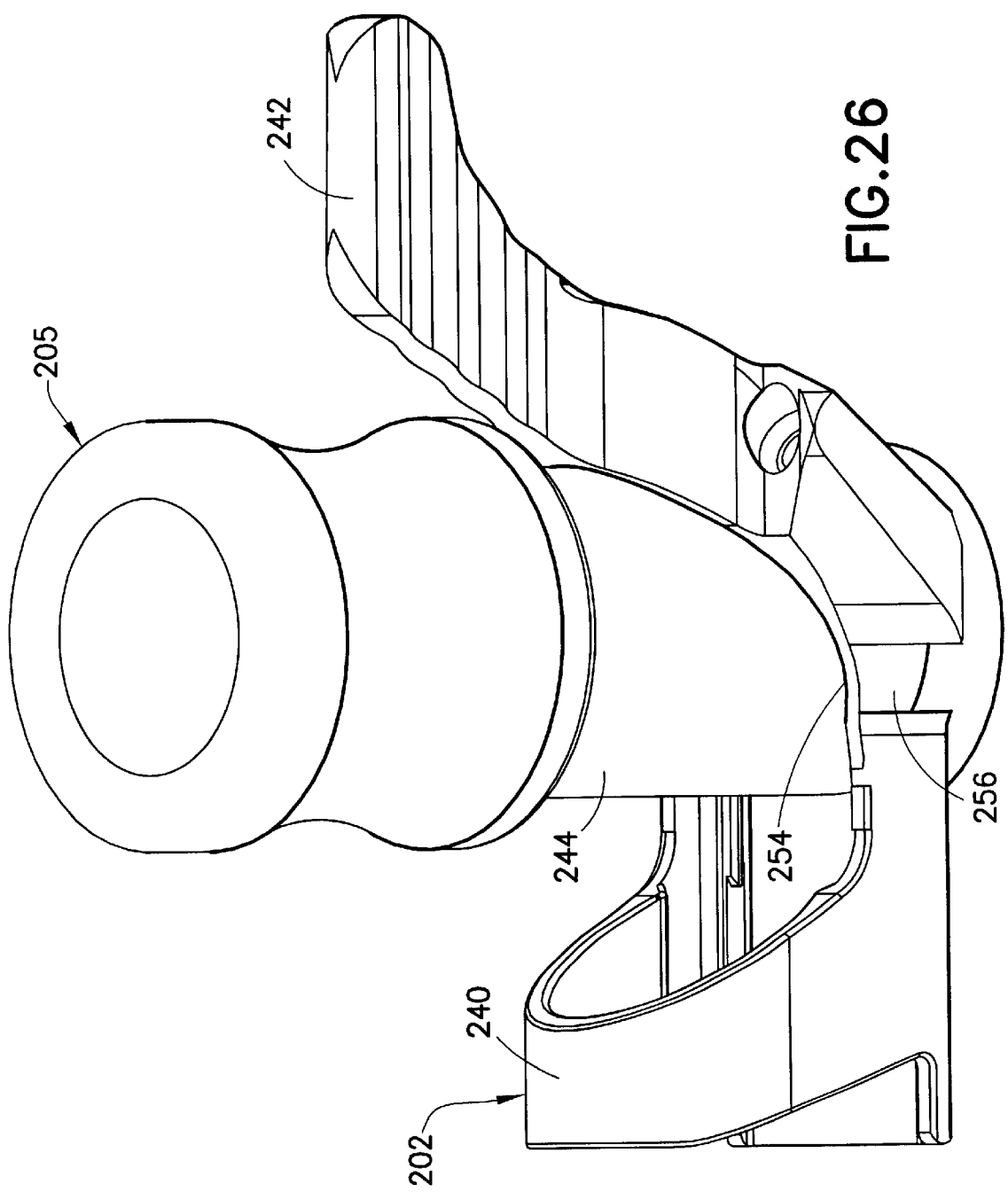

KERATOME WITH SUSPENDED STABILIZED BLADE, IMPROVED SUCTION RING WITH APPLANATOR AND GUIDED ENGAGEMENT WITH KERATOME CUTTER HEAD, AUTOMATED TRANSLATION OF THE CUTTER HEAD, AND BLADE INSERTION TOOL

This application is a continuation-in-part of application Ser. No. 09/178,282 filed Oct. 23, 1998 now abandoned which claimed priority to Provisional Application Serial No. 60/063,083 filed Oct. 24, 1997, and this application also claims priority to Provisional Application No. 60/107,187 filed Nov. 5, 1998.

FIELD OF THE INVENTION

The invention herein relates to a keratome having a cutter head with a suspended stabilized reciprocating blade, an improved suction ring accepting an applanator and with entrance and cutting guideways for presenting and applying the cutter head and its suspended blade to the cornea, drive means for automated translation of the cutter head, and blade insertion cooperating with the cutter head.

BACKGROUND OF THE INVENTION

A keratome is an instrument used in ophthalmic surgery and, more particularly, in surgery to reshape the cornea for vision correction. A keratome incises a generally spherical segment of the cornea except for a connecting hinge. The cornea segment is lifted and held aside while the exposed truncated cornea surface is shaped for vision correction. Thereafter, the spherical cornea segment is repositioned to cover the shaped, truncated cornea surface. The cornea segment heals to the shaped surface, resulting in a reshaped cornea that acts as a corrective lens.

It will be appreciated that a keratome must achieve an accurately positioned, surgically precise cut with minimal tissue damage to enhance the healing process. Further, the cut must remain uncontaminated, also to aid the healing process and avoid irritation and infection.

In accurately positioning and performing a cornea cut, it is known to use a suction ring as an interface with the eye. Suction is used to temporarily secure the suction ring to the eye in a desired position. Typically, a suction ring is secured to the sclera, near the periphery of and surrounding the cornea.

It is also desirable to measure the cornea and coordinate the extent of the incision with the size of cornea in order to remove a properly sized cornea segment and to provide an appropriate hinge in conjunction with the excised cornea segment.

It is also known to apply a cutting instrument with the suction ring. Thus, the suction ring positions and presents the cutting instrument with respect to the cornea. Clearly, if any slippage or disengagement of the suction ring occurs, a correspondingly inaccurate cut may also occur. Present suction rings occasionally do experience slippage or disengagement, and it is believed this occurs because of a poor interface with the surface of the sclera resulting in loss of suction or uneven suction along various segments of the ring. Currently, engagement of a cutting instrument with a suction ring is often difficult to achieve, because the engagement must be precise, making the engagement difficult to initiate.

Precision of the cornea cut requires proper positioning of a cutting instrument with respect to the cornea, which is achieved by the location and secure attachment of the suction ring, and also requires a very smooth operating cutting blade. Cutting instruments often use a reciprocating cutting blade to achieve a smooth, precise incision. Any flutter in the operation of the reciprocating cutting blade can cause a somewhat ragged incision, with consequent difficulties in replacing the cornea segment and smooth healing thereof.

The cornea cut must also remain uncontaminated, because any foreign matter in the incision may become encapsulated and cause irritation and possible infection. Cutting instrument designs which support a cutting blade on a bearing surface adjacent the area of the incision increase the risk of contamination. Contact between the cutting blade and the bearing surface creates friction and wear. This not only heats the cutting blade, but also sloughs off microscopic metal wear particles. These may lodge in the cornea incision, with undesirable effect.

It is also desirable to translate the cutting instrument across the cornea in a smooth manner and to reliably stop the translation of the cutting instrument at the furthest extent of the cut. Non-damaging withdrawal of cutting instrument is also desirable.

There is also a need to quickly and easily load blades into the cutting instrument, and to remove blades after use.

Therefore, there is a need for a keratome including a suction ring that easily, accurately and securely positions a cutting instrument with respect to the cornea and that provides a surgically precise, uncontaminated incision of a cornea segment. There is an additional need for improved automation in making the incision.

SUMMARY OF THE INVENTION

Accordingly, it is a principal object of the invention herein to provide a keratome for ophthalmic surgery.

It is an additional object of the invention herein to provide a keratome that achieves accurate and secure engagement with the eye.

It is another object of the invention to provide a keratome that facilitates accurate, pre-cut measurement of the cornea.

It is also an object of the invention to provide a keratome including a cutting instrument that is easily and accurately engageable with a suction ring secured to the eye.

It is an additional object of the invention to provide a keratome with automated translation of a cutting instrument across a suction ring.

It is a further object of the invention to provide a keratome that achieves an accurate and smooth cut.

It is another object of the invention to provide a keratome that avoids contamination of the incision made on the cornea.

It is also an object of the invention to provide a keratome with simple and efficient changing of the blade in a cutting instrument.

According to general aspects of the invention herein, a keratome generally comprises a suction ring and a cutting instrument having a cutter head guided into precision sliding engagement with the suction ring, the cutter head including a suspended, reciprocating blade. An applanator is receivable on the suction ring for measuring the segment of cornea to be cut, and the cutting instrument is adjustable or preset for length of cut.

Also according to aspects of the invention, a keratome generally comprises a cutting instrument having a cutter head including a reciprocating blade with a cutting edge extending below a sole surface, and a suction ring. The suction ring includes an eye ring adapted to be secured to an eye by suction and defines a cornea aperture presenting the cornea of the eye for cutting a cornea segment. The suction ring furthers includes a shoe from which the eye ring extends, the shoe defining a cutting guideway configured for receiving the cutter head in precision mating sliding engagement for passing the cutting edge of the cutter blade over the cornea aperture and thereby incising a cornea segment. The shoe further defines an entrance guideway extending from and generally aligned with the cutting guideway, the entrance guideway configured for receiving the cutter head in orienting sliding engagement positively positioning the cutter head into the aforesaid precision mating sliding engagement in the cutting guideway.

According to additional aspects, the cutter head defines two tongues extending downwardly at the edges of its sole surface, and the cutting guideway includes two guide grooves respectively receiving the tongues. The cutting guideway guide grooves are fully defined at the transition between the entrance guideway and the cutting guideway. According to further aspects, the entrance guideway is partially defined by a guide hoop of the shoe, and the cutter head is cooperatively shaped to enter the guide hoop and progressively orient the cutter head for entry to the cutting guideway. The guide hoop is preferably positioned substantially at the transition between the entry guideway and the cutting guideway. Also, according to further aspects, the entrance guideway includes curbs upstanding along the marginal edges of an entrance ramp portion of the shoe for generally aligning the cutter head with the guide hoop, the shoe defines side rails extending from the guide hoop, and the cutter head has side rail pockets slidingly receiving the side rails. Thus, there are multiple points of contact between the cutter head and the shoe defining the entrance guideway, serving to align the cutter head for sliding movement in the cutting guideway. The foregoing configurations of the cutter head and suction ring provide easy engagement and accurate positioning of the cutter head within the suction ring.

Referring to another aspect, the suction ring includes a handle and the handle is preferably positioned opposite the entrance guideway of the suction ring, for manual stabilization of the suction ring and coordination of the suction ring and cutting instrument during introduction of the cutting instrument.

According to still other aspects in the invention, a suction ring includes an eye ring defining a cornea aperture and a shoe, and the shoe defines a socket for receiving and positioning an applanator with a measuring surface in contact with a cornea of an eye presented through the cornea aperture, for measuring the size of the cornea to be incised. Cooperating stop means are provided between the suction ring and cutting instrument for adjusting the extent of the incision according to the applanator measurement of the cornea.

According to a still further aspect of the invention, the cutting instrument includes a stop which butts against the suction ring at a desired extent of incision. The stop is preferable a rotatable collar adjustably presenting one of a plurality stops for selectively setting different extents of incision.

According to additional aspects, a suction ring includes an eye ring with outer and inner contact surfaces shaped to engage the eye, and a suction channel defined between the inner and outer contact surfaces. The suction channel additionally defines a secondary distribution channel and a suction conduit opens to the suction channel and the secondary distribution channel. The secondary distribution channel ensures delivery and equalization of suction about the eye ring for secure attachment to the eye.

Also according to aspects of the invention herein, the cutting instrument includes a cutter head having a blade assembly. The blade assembly includes a metal cutting blade mounted to and extending from a blade holder to a cutting edge. The blade holder is preferably fabricated of a polymer, such as nylon. The blade holder defines a drive track transverse to the cutter blade and its cutting edge. The cutter head further defines a blade cavity generally accommodating and supporting the blade holder for reciprocal sliding movement. The cutter head defines a blade slot accommodating the cutting blade and extending to a blade opening from a foot of the cutter head, adjacent which the cutting edge is deployed for incising the cornea. The cutting blade is suspended with respect to and does not contact the cutter head. The cutter head defining the blade cavity is preferably of unitary, one-piece construction, but may also be comprised of a base and a cap together defining the blade cavity.

The blade cavity includes a guide bar cooperating with a guide slot formed in the blade holder. According to one aspect of the invention, the guide is a linear guide bar received in the guide groove formed in the blade holder, and configured for thin line contact between the guide bar and the guide groove. According to another aspect of the invention, the guide bar is comprised of two spaced apart post projections received in the guide slot, which is parallel to the cutting edge of the blade.

According to additional aspects of the invention, the blade cavity defines one of a guide slot or guide bar, and the blade holder defines the other of the guide slot or guide bar, the guide bar extending into the guide slot in closely conforming mating sliding engagement to guide and stabilize the blade holder in its reciprocal movement within the cutter head. In a more particular aspect of the invention, the cutter head defines a substantially rectangular guide bar, and the blade holder defines a substantially rectangular guide slot accommodating the guide bar. The guide slot has an incrementally smaller width than the guide bar to preload the blade holder on the guide bar. The guide bar, and additional surfaces of the blade cavity, may be treated with a lubricous coating such as a nickel/Teflon® coating, to provide smooth reciprocation.

The cutter head further includes a blade shield and foot, the foot having projecting tongues for slidingly engaging the guide grooves of the shoe portion of the suction ring. The cutter head is characterized in that it does not contact the cutting blade, which is suspended extending from the blade holder. The cutting edge of the blade extends a selected distance below a forward or toe surface of the foot to establish a uniform depth of cut.

According to one aspect of the invention, the cutter head includes a view port as part of the foot, for visually monitoring passage of the cutter head and blade over the cornea and the cut.

In some aspects, the cutting instrument further includes a handle drive, to which the cutter head is secured. The handle drive has a drive shaft extending through the cutter head and terminating in an eccentric drive pin received in the drive track of the blade holder. A handle drive turbine is used to rotate the drive shaft at high rpm, which according to one aspect of the invention is between 8,000 and 16,000 rpm, and thereby reciprocate the blade holder and blade. The drive shaft is supported on bearings and located to isolate application of the drive force to the blade holder through the drive pin, in cooperation with the cutter head.

According to further aspects, the cutting instrument is reciprocally mounted in an automated drive unit. The automated drive unit is engageable with the suction ring, and the automated drive unit has drive means for advancing the cutting instrument and its cutter head across the suction ring and for retracting the cutting instrument and cutter head after incising a cornea segment of an eye. The automated drive unit is removably secured to the suction ring and can be introduced in the suction ring after the suction ring is secured on the eye. Thus, the suction ring is attached without the bulk of the automated drive unit and its cutting instrument, and the automated drive unit and associated cutting instrument and cutter head are easily joined to the suction ring for cutting.

Also, according to aspects, the automated drive unit has a threaded shaft and worm gear and includes a motor powering the threaded shaft to translate the cutting instrument and cutter head. The motor may be an electric motor, and an electrical spike at the limit of travel may be used to reverse the direction of the cutting instrument and cutter head for automated withdrawal. The cutting instrument may be inactivated during withdrawal.

According to other aspects, the cutting instrument includes a tubular body with a motor and a cutter head, and the cutter head mounts to the tubular body by means of a mounting shank and a bayonet shaped groove which positively orients the cutter head with respect to the tubular body. The bayonet style groove also provides for quick mounting and dismounting of the cutter head. According to additional aspects of the invention, the motor of the cutting instrument is connected to a drive shaft for reciprocating a cutter blade in the cutter head, the connection being achieved by a coupling including a drive coupling member having ears received in mating slots of a positioning coupling member, and a positioning coupling member having pointed ears for guiding the drive ears into the mating slots.

According to further aspects of the invention, the keratome is provided with a blade insertion tool which includes a shaft retractor for retracting the drive pin of a blade drive shaft from the cutter head blade cavity to provide clearance for inserting the blade, and an injector for inserting a cutter blade into the blade cavity and for displacing a used cutter blade out of the blade cavity.

Other objects, aspects and features of the invention will in part be understood by those skilled in the art and will in part appear from a perusal of the following description of the preferred embodiments and the claims, taken together with the drawings.

BRIEF DESCRIPTION OF THE DRAWINGS

FIG. 5 is a bottom perspective view of the suction ring of the keratome of FIG. 1;

FIG. 6 is a top perspective view of the suction ring of the keratome of FIG. 1;

FIG. 7 is a side elevation view, partially in section, of the suction ring of the keratome of FIG. 1;

FIG. 8 is a perspective view of the suction ring of the keratome of FIG. 1, and a schematic view of apparatus for applying suction to the suction ring;

FIG. 10 is a perspective view of the cutter head body of the cutting instrument of FIG. 9;

FIG. 26 is a perspective view of the suction ring and applanator of FIG. 18;

The same reference numbers refer to the same elements throughout the various figures.

DESCRIPTION OF PREFERRED EMBODIMENTS

Figure 1:
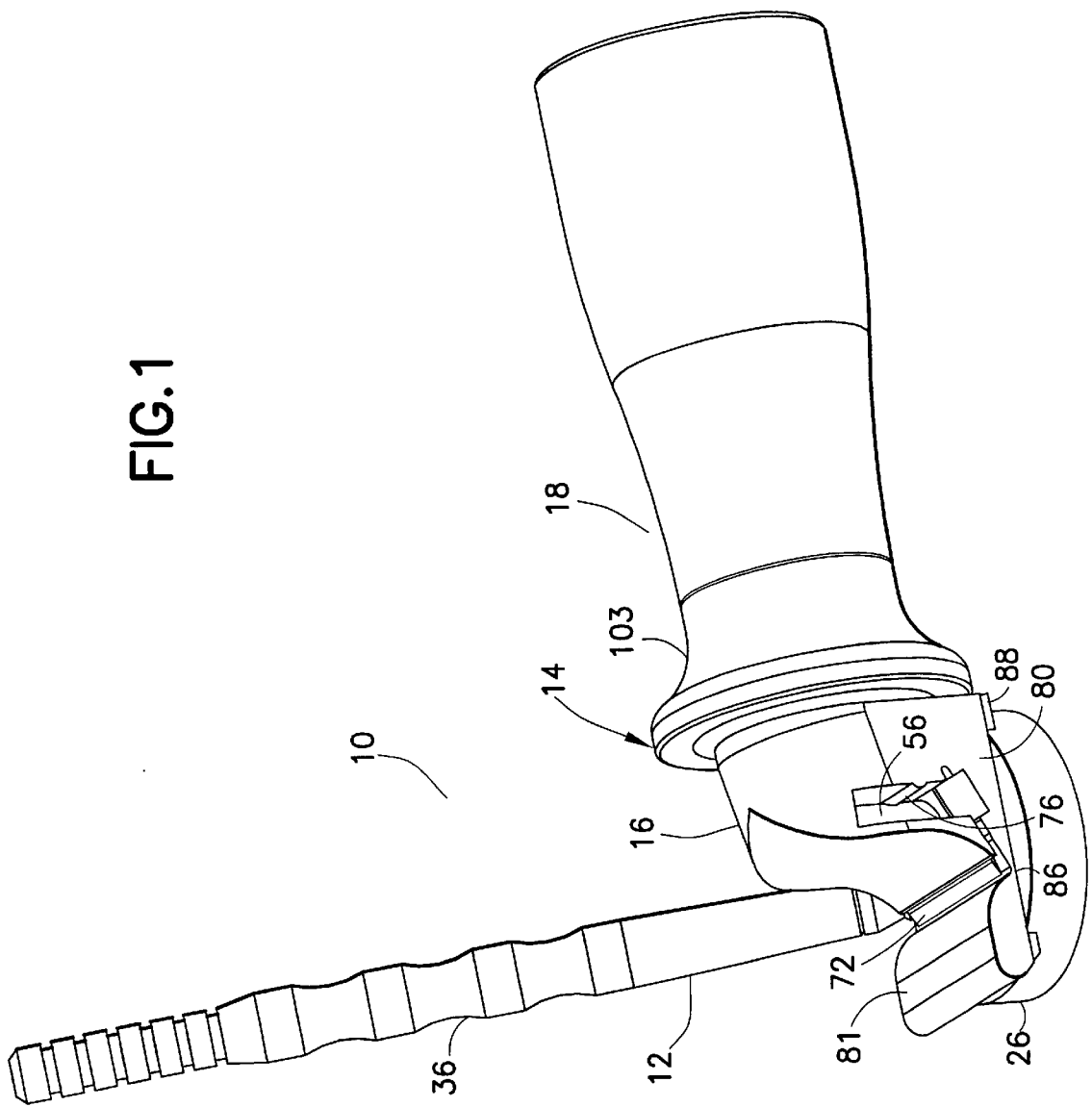
FIG. 1 is a perspective view of a keratome according to the invention herein, including a suction ring and a cutting instrument having a cutter head and handle drive.

With reference to FIGS. 1–13, there is illustrated a keratome 10 according to the invention herein that is used in ophthalmic surgery for removing a cornea segment. The keratome 10 generally comprises a suction ring 12 and a cutting instrument 14, which in turn generally comprises a cutter head 16 and a handle drive 18. Various views of the keratome 10 are illustrated in FIGS. 1, 2 and 3, and FIG. 4 illustrates the keratome 10 removing a cornea segment 20 from the cornea 22 of an eye 24. Before discussing the keratome 10 and its operation in detail, the various component parts will be individually described.

Figure 4:
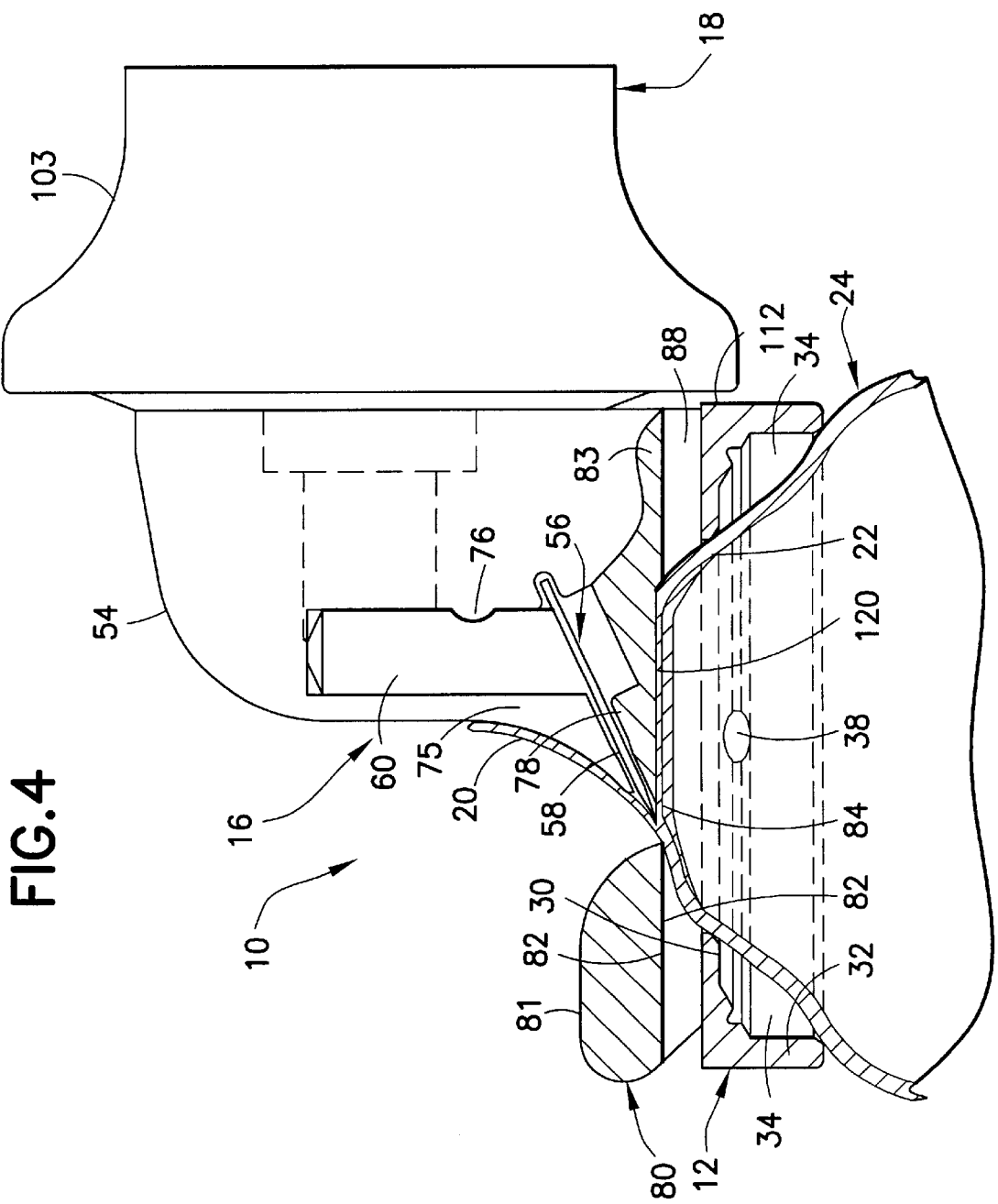
FIG. 4 is a side elevation schematic view, partially in section, of the keratome of FIG. 1, shown incising a corneal segment.

FIGS. 5–7 depict various views of the suction ring 12. The suction ring 12 includes an eye ring 26 having a generally L-shaped cross-section as best seen in FIG. 7. The eye ring 26 defines a cornea aperture 28 and defines a first annular inner eye contact surface 30 adjacent the cornea aperture 28. The eye ring 26 further defines a second, annular outer eye contact surface 32 which is spaced apart from the first inner contact surface 30, with a suction channel 34 defined therebetween. As best seen in FIG. 4, the contact surfaces 30 and 32 engage with the exterior of the eye, wherein the surface of the eye also defines the suction channel 34. The contact surfaces 30 and 32 are angled and curved to conform to the contour of the eye, thereby insuring good engagement with and sealing to the eye.

The suction ring 12 further comprises a conduit stem 36 having a conduit opening 38 for providing suction to the suction channel 34. The conduit stem is mounted through the eye ring 26 so that the conduit opening 38 communicates with the suction channel 34. In some instances, the eye could be deformed to block the opening 38 or the suction channel 34, and if this occurs the suction is weakened and the suction ring may disengage or slip relative to the eye. To prevent this, the eye ring 26 further defines a secondary distribution channel 40 extending inwardly from the suction channel 34 and intersecting the conduit opening 38. The distribution channel 40 is sufficiently deep and narrow at its opening that the eye cannot block it, and it assures that equal suction is provided around the entire periphery of the eye ring.

The suction ring also defines a shoe 42 from which the eye ring depends. The shoe 42 is configured for receiving the cutter head 16, the shoe 42 comprising the flat surface 43 flanked by two guide grooves 44 and 45, the entrances to which are flared outwardly.

With reference to FIG. 8, a pump 46 develops negative pressure, also referred to as suction, through a conduit 47 having an accumulator 48 therein. A valve 49 controls application of the suction to the suction ring 12, and a gauge 50 provides an indication of the suction. The valve 49 may include provision for foot pedal operation, if desired. A filter 51 is also preferably provided. The conduit 47 is attached to the conduit stem 36 of the suction ring 12, to apply the suction to the suction channel 34 and secondary distribution channel 40.

It will be appreciated that the eye ring 26 is applied to the eye with the cornea positioned in the cornea aperture 28 and is secured to the eye by application of suction. The suction ring 12 provides a fixed base for applying the cutting instrument 14, which is received on the shoe 42, as more fully discussed below.

With reference to FIGS. 9–14, the cutting instrument 14 of the keratome 10 includes the cutter head 16 and handle drive 18. The cutter head 16 includes a body 54, shown in FIG. 10, and a blade assembly 56, with a blade 58 and a blade holder 60 of the blade assembly 56 being shown in FIGS. 11 and 12, respectively. The blade holder 60 is a shaped nylon body having a mounting stud 62 extending from the bottom thereof, and the blade 58 has an opening 64 which is received surrounding the mounting stud 62 to mount the blade on the blade holder, with the blade extending therefrom to a cutting edge 72. The blade holder 60 defines a guide slot 68 which extends across the back surface 66, parallel to the blade 58 and its cutting edge 72, and the back surface 66 further defines a drive track 70, perpendicular to the guide slot 68. The cutting edge 72 of the blade extends oppositely from the back surface 66 of the blade holder as seen for instance in FIGS. 3, 4 and 9.

Figure 13:
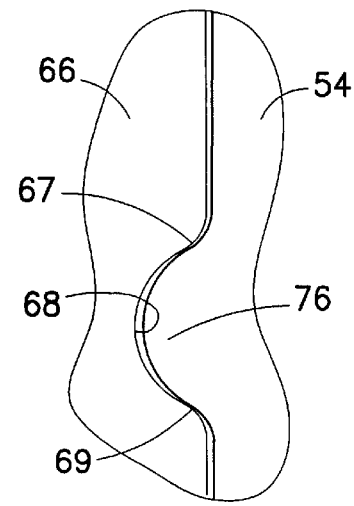
FIG. 13 is a segmental side elevation view of the cutter head, showing an interface of the blade holder of FIG. 12 and cutter head body of FIG. 10.

The body 54 of the cutter head 16 is a one-piece, unitary structure defining a blade holder cavity 74 which closely embraces and guides the blade holder 60, but permits the blade 58 suspended from blade holder 60 to operate free from contact with the cutter head body 54. More particularly, the cutter head includes a guide bar 76 which is received in the guide slot 68 in the back surface 66 of the blade holder 60, and the top of the blade holder and front surface of the blade holder also are slidingly engaged within the blade holder cavity 74. With particular reference to FIG. 13, the guide bar 76 and the groove 68 are shaped so that there is contact 67 and 69 at the corners of the guide bar 76 and guide slot 68, which provide for guiding the blade holder in transverse reciprocating motion with a minimum of binding, friction or blade flutter.

Figure 9:
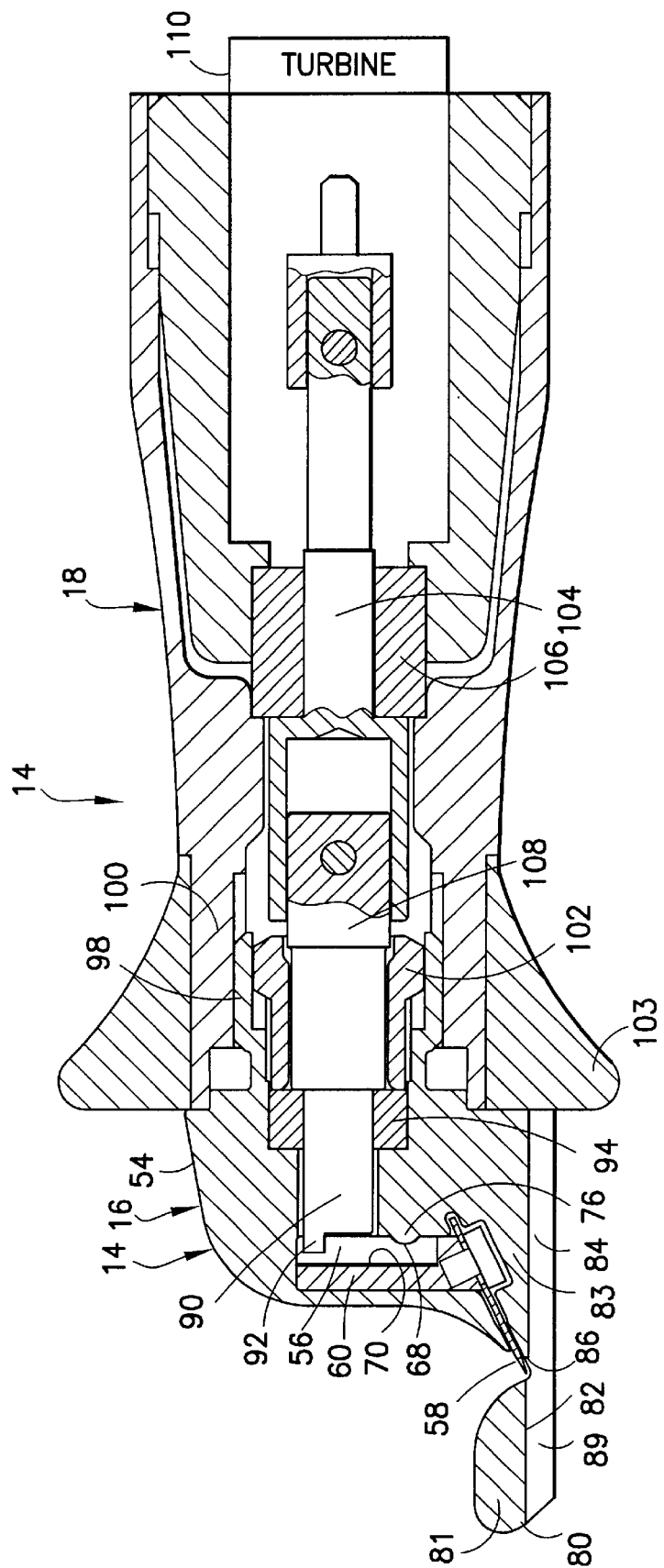
FIG. 9 is a longitudinal view, partially in section, of the cutting instrument of the keratome of FIG. 1.
Figure 11:
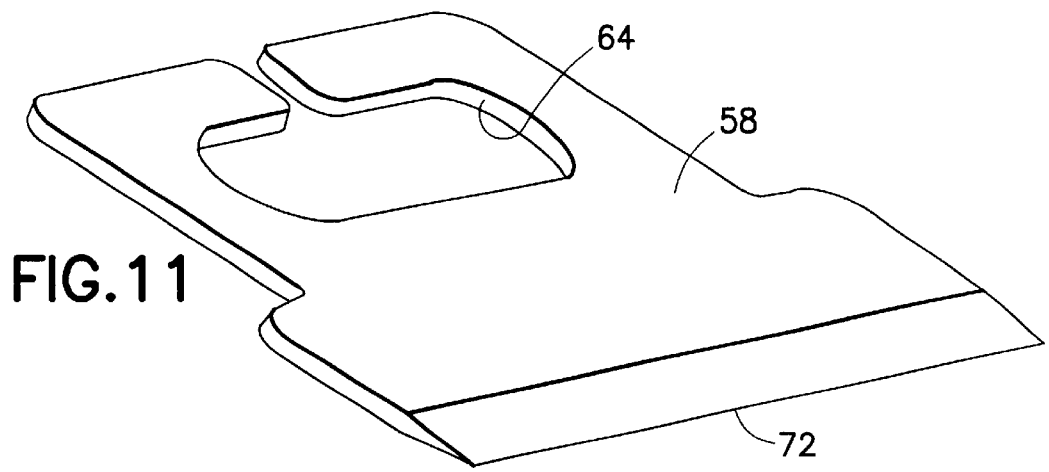
FIG. 11 is a perspective view of a cutting blade of a blade assembly of the cutting instrument of FIG. 9.
Figure 12:
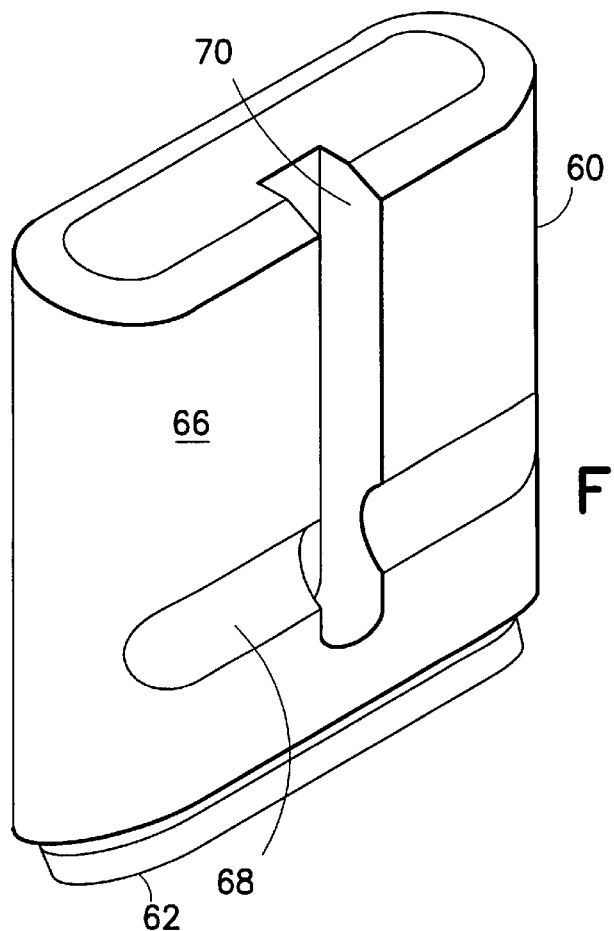
FIG. 12 is a perspective view of a blade holder of a blade assembly of the cutting instrument of FIG. 9.

As best seen in FIG. 9, the cutter head 16 further comprises precision bearings 94, which receive a drive shaft 90 extending from the handle drive 18 and having a drive pin 92 eccentrically located on the end thereof. The drive pin 92 extends into the drive track 70, so that when the drive shaft 90 is rotated, the drive pin 92 reciprocates the blade assembly 56. The drive shaft 90 is supported on precision bearings 94 which limit the extension of the drive shaft and drive pin into the blade cavity 74 in order to prevent the end of the drive shaft from contacting the blade holder and creating friction and binding.

The body 54 of the cutter head 16 further defines a blade slot 78 extending from the blade holder cavity 74, in which the blade 58 is suspended by the blade holder without touching the body 54. A blade shield portion 75 of the body 54 is located above the suspended blade.

Figure 2:
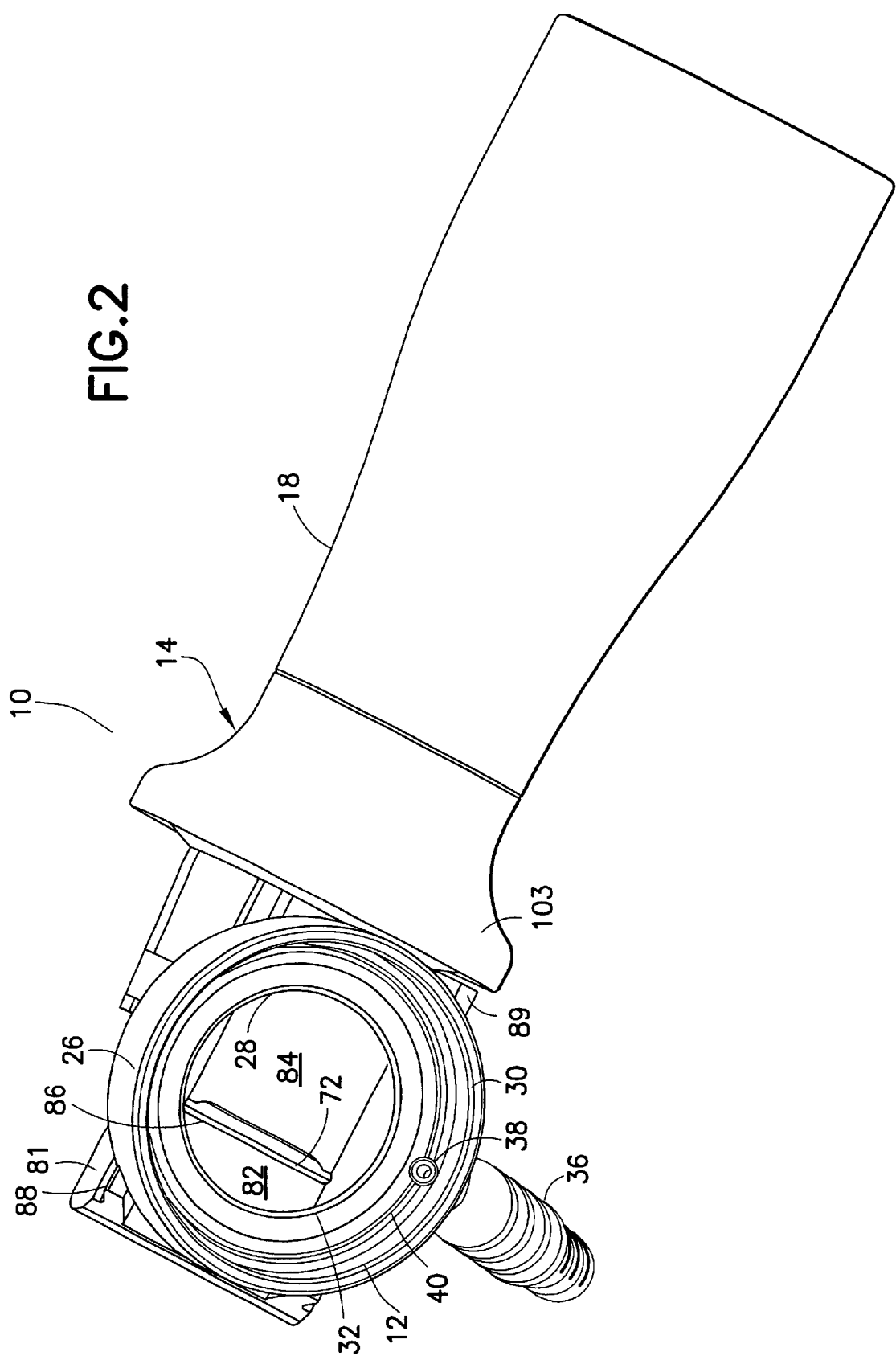
FIG. 2 is a bottom perspective view of the keratome of FIG. 1.
Figure 3:
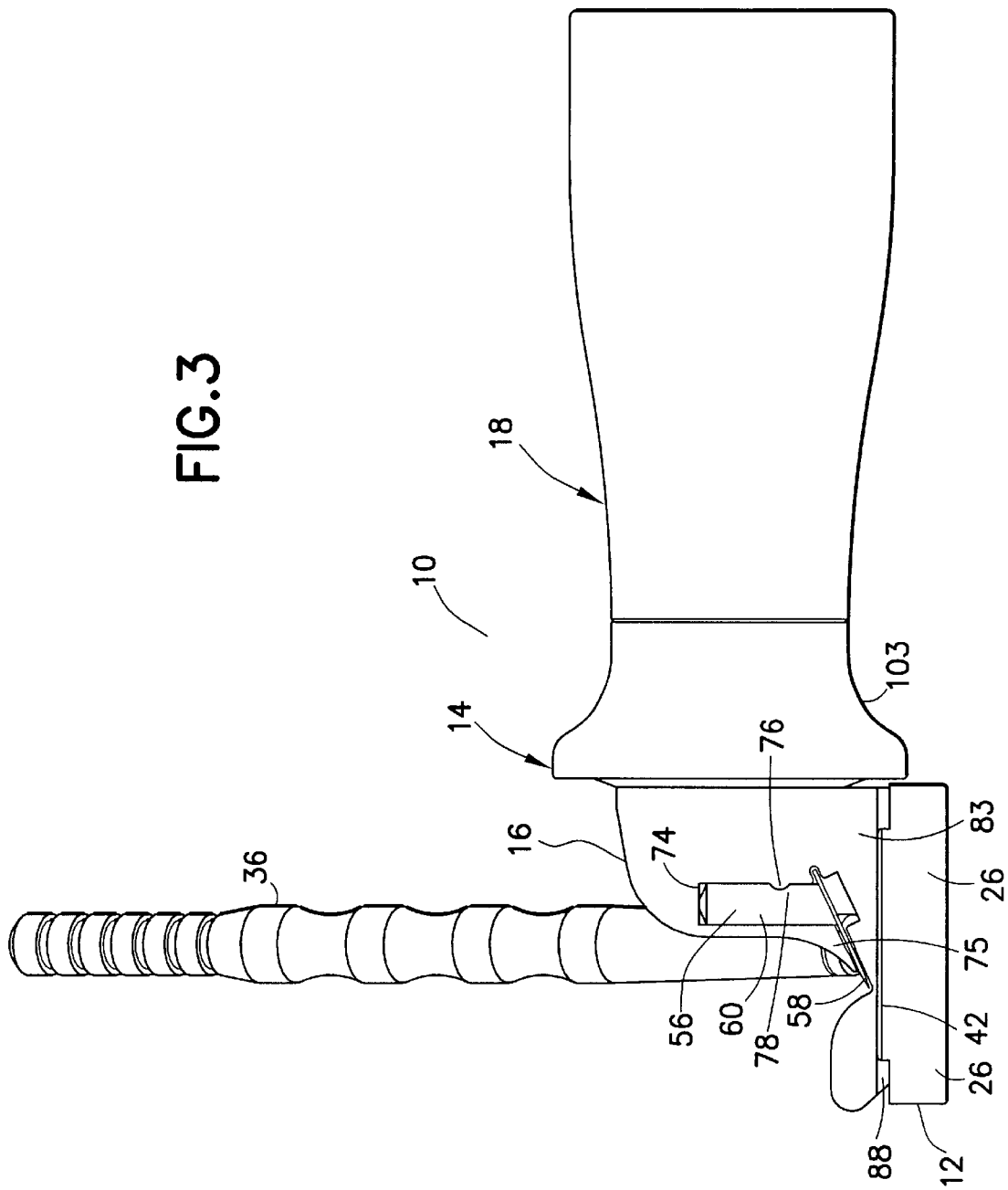
FIG. 3 is a side elevation view of the keratome of FIG. 1.
Figure 14:
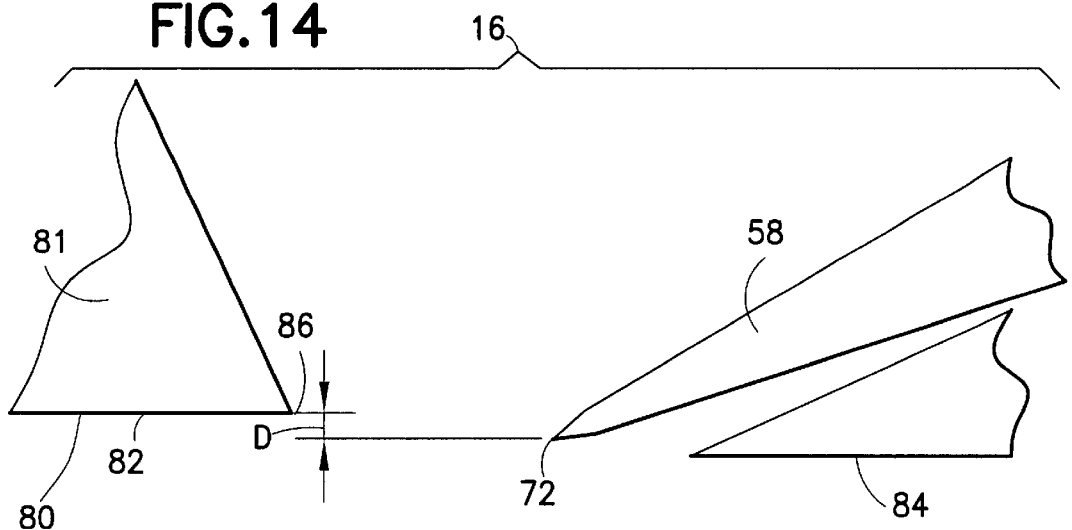
FIG. 14 is an enlarged segmental view of the cutting instrument of FIG. 9, showing the depth of cut of the blade.

The body 54 further defines a foot 80 having a blade opening 86, through which the cutting edge 72 of the blade 58 protrudes, as best seen in FIGS. 2, 4, and 14. The foot 80 includes a toe portion 81 having a first sole surface 82 and heel portion 83 with a second sole surface 84, separated from the first sole surface 82 by blade opening 86. The blade opening 86 is formed where the blade slot 78 intersects the sole. The sole surfaces 82 and 84 are flanked by projecting tongues 88 and 89 which are respectively received in the guide grooves 44 and 45 of the suction ring 12. Thus, the cutter head 16 is engageable with the shoe 42 of suction ring 12 to pass the cutting edge 72 of cutter blade 58 across the cornea, as best seen in FIGS. 1–4. It will be appreciated that the cutter head 16 may pass in either direction on the suction ring 12, and that the suction ring may be engaged with either eye, as required to achieve clearance from the nose.

The blade assembly 56 is inserted in and removed from the cutter head by first disengaging the drive pin, and then sliding the blade assembly in and out of the blade holder cavity 74.

With reference to FIGS. 4 and 14, the first sole surface 82 of the cutter head 16 is stepped upwardly from the second sole surface 84, and the blade 58 extends through the blade opening 86 so that its cutting edge 72 is below sole surface 82. When the suction ring 12 is attached, the cornea extends upwardly through the cornea aperture 28 and is pressed against the sole surfaces of the cutter head as the cutter head passes over the cornea aperture. The cornea is thereby cut to a depth D determined by the extension of the cutting edge 72 of cutter blade 58 below sole surface 82. The lower, second sole surface 84 also supports the cornea, including the truncated surface thereof, and assists in presenting and stabilizing the cornea with respect to the blade edge 76 for cutting.

Figure 15:
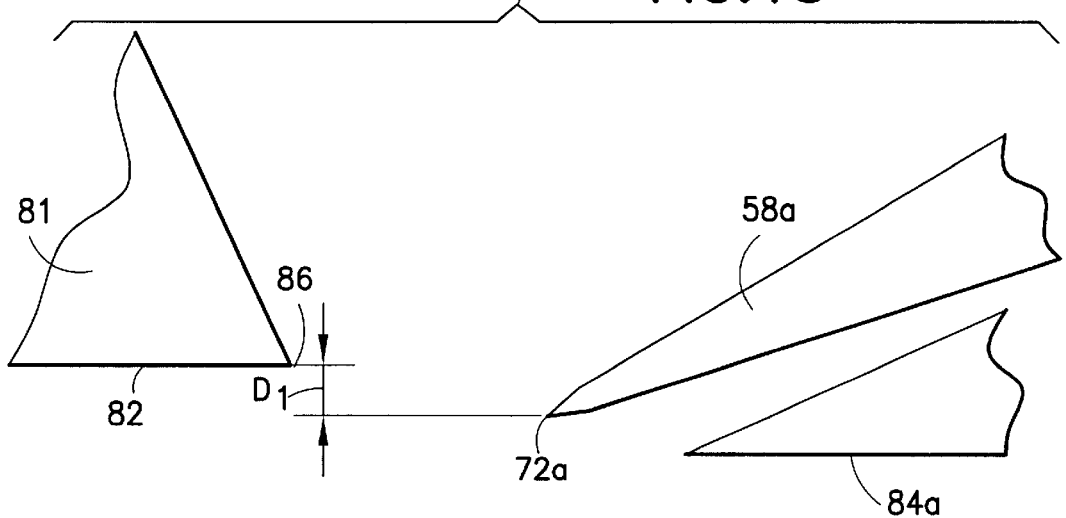
FIG. 15 is an enlarged segmental view of a modified cutting instrument similar to FIG. 9, providing another depth of cut.
Figure 16:
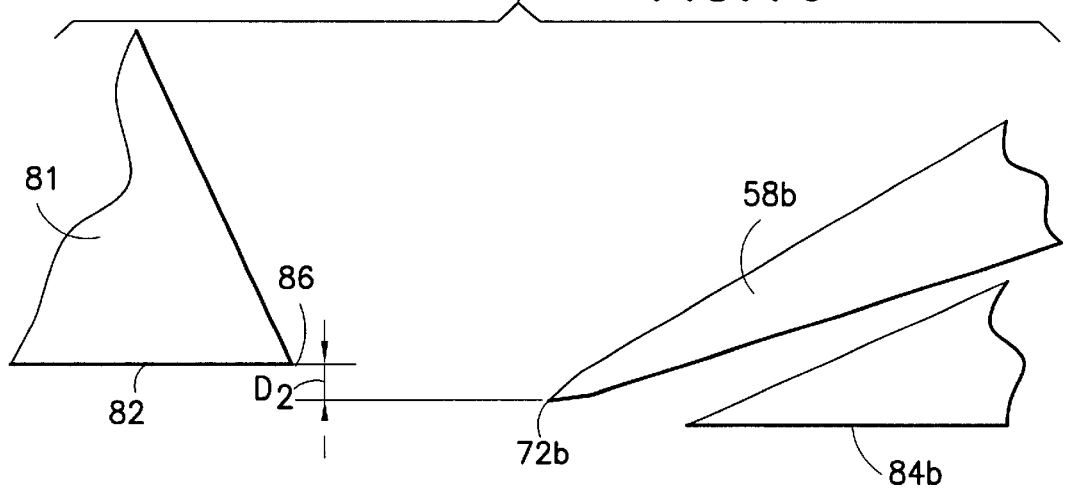
FIG. 16 is an enlarged segmental view of a modified cutting instrument similar to FIG. 9, providing another depth of cut.

With reference to FIGS. 15 and 16, portions of modified cutter heads 16a and 16b are shown in enlarged segmental section similar to FIG. 14. Cutter heads 16a and 16b are respectively provided with cutting blades 58a and 58b being respectively longer and intermediate the blade 58 shown in FIG. 14, so that their cutting edges 72a and 72b provide for deeper cuts D1 and D2 incising thicker cornea segments, as dictated by the requirements of a particular eye and procedure. The trailing sole surfaces 84a and 84b are also preferably lowered to cooperate respectively with the longer blades in providing a deeper cut. Although it is preferred to utilize a modified head to provide a deeper cut, it will be appreciated that one of the longer blades 58a or 58b can be used with cutter head 16 to provide a deeper cut than the blade 58.

With reference to FIG. 9, the cutter head 16 is supported on and the blade assembly 56 is reciprocally driven by the handle drive 18. The handle drive 18 includes a generally tubular body 100 which is secured to a mounting shank 98 of the cutter head 16 by cooperating mating quadralead threads 102. A flared collar 103 is positioned adjacent the cutter head, providing a comfortable control grip and also functioning as a stop, as further discussed below. The handle drive 18 also has a drive shaft 104 supported on bearings 106 and axially slidably coupled at 108 with respect to the drive shaft 90.

The handle drive further includes a turbine 110 which is driven by compressed air, which may be supplied by pump 46, and rotates the drive shafts 104 and 90 at approximately 8,000 to 16,000 rpms. Therefore, the cutter blade 58 makes full reciprocal cycles at the same frequency.

With reference to FIG. 4, operation of the keratome 10 is illustrated. The suction ring 12 is positioned and engaged on eye 24 as described above, and the foot 80 of the cutter head 16 is engaged with the shoe of the suction ring by sliding tongues 88,89 into guide grooves 44,45. By advancing the cutter head 16 across the suction ring, the cornea is presented to the cutting edge 72 of blade 58. The cornea engages the forward sole surface 82, on the toe 81 of the foot of the cutter head, prior to presentation to the cutting edge 72. Because the edge 72 of the cutting blade is disposed below the sole surface 82 by a fixed depth D, the edge of the cutting blade thereby engages and incises a cornea segment 20. The blade shield portion 75 of the cutter head 16 lifts the cornea segment 20 and separates it so that a smooth cut may proceed. The rear or heel sole surface 84 supports the truncated portion of the cornea as indicated at 120, also stabilizing the cornea as the cut proceeds. The toe may include a transparent insert so that the progress of the cutter head across the cornea may be seen. The extent of the incision is limited by the abutment of flared collar 103 against suction ring 12, which occurs generally at 112, providing for a hinge portion of the cornea connecting cornea segment 20 to the cornea 22.

The cutting blade is disposed at an angle of approximately twenty-five degrees (25°) with respect to the sole surfaces of the cutter head, and it has been found that this angle produces a smooth and accurate cut. The angle, however, is not believed to be critical.

With continued reference to FIG. 4, the cutting blade 58 does not touch the body 54 of the cutter head, but is positioned by the blade holder 60 in a suspended relationship to the surrounding structure. Therefore, there is no friction and wear generated between the cutting blade 58 and the cutter head body 54, and no debris is created which would contaminate the incision.

The handle drive 18 extends rearwardly from the cutter head 16 in substantially parallel relationship to the direction of the motion of the cutter in performing an incision, and it has been found that this is a comfortable and controllable orientation of the handle for the surgeon. Upon completion of the cut, the cutting instrument 10 is withdrawn from the suction ring 12 and the suction ring 12 may then be released from the eye in accordance with further aspects of the surgical procedure.

Figure 17:
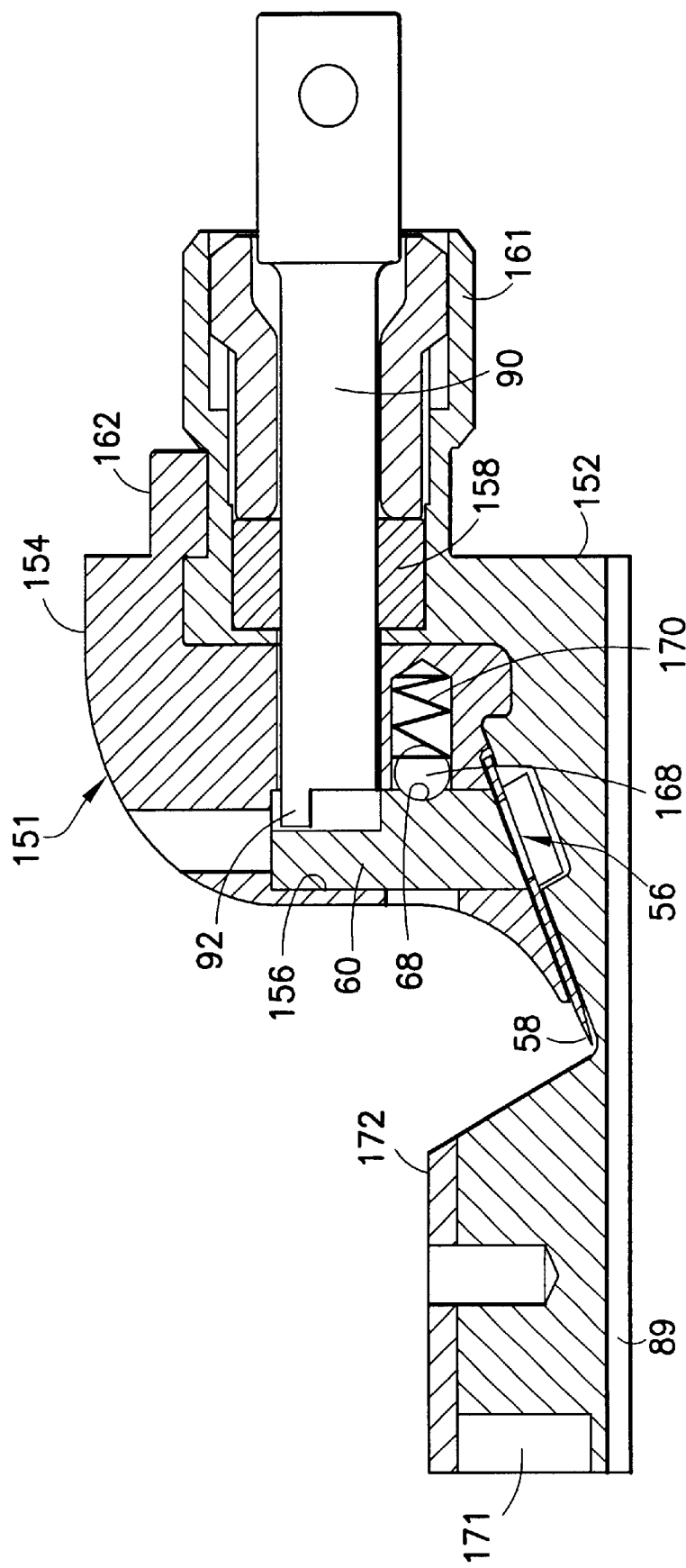
FIG. 17 is a side elevation view of an additional cutting instrument of a keratome according to the invention herein, incorporating a cutter head with a two-piece body.
Figure 18:
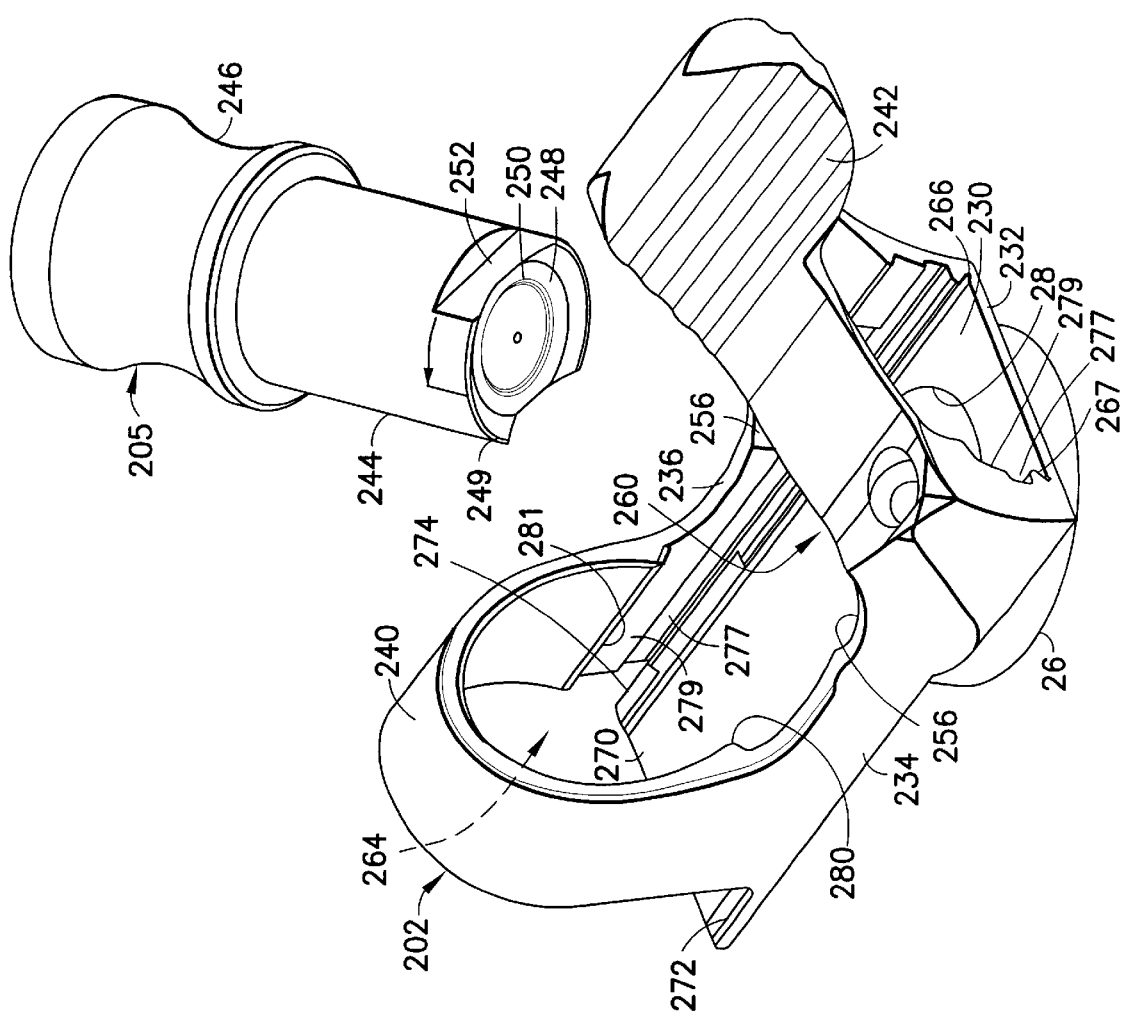
FIG. 18 is a perspective view of a suction ring and applanator of another keratome according to the invention herein.
Figure 19:
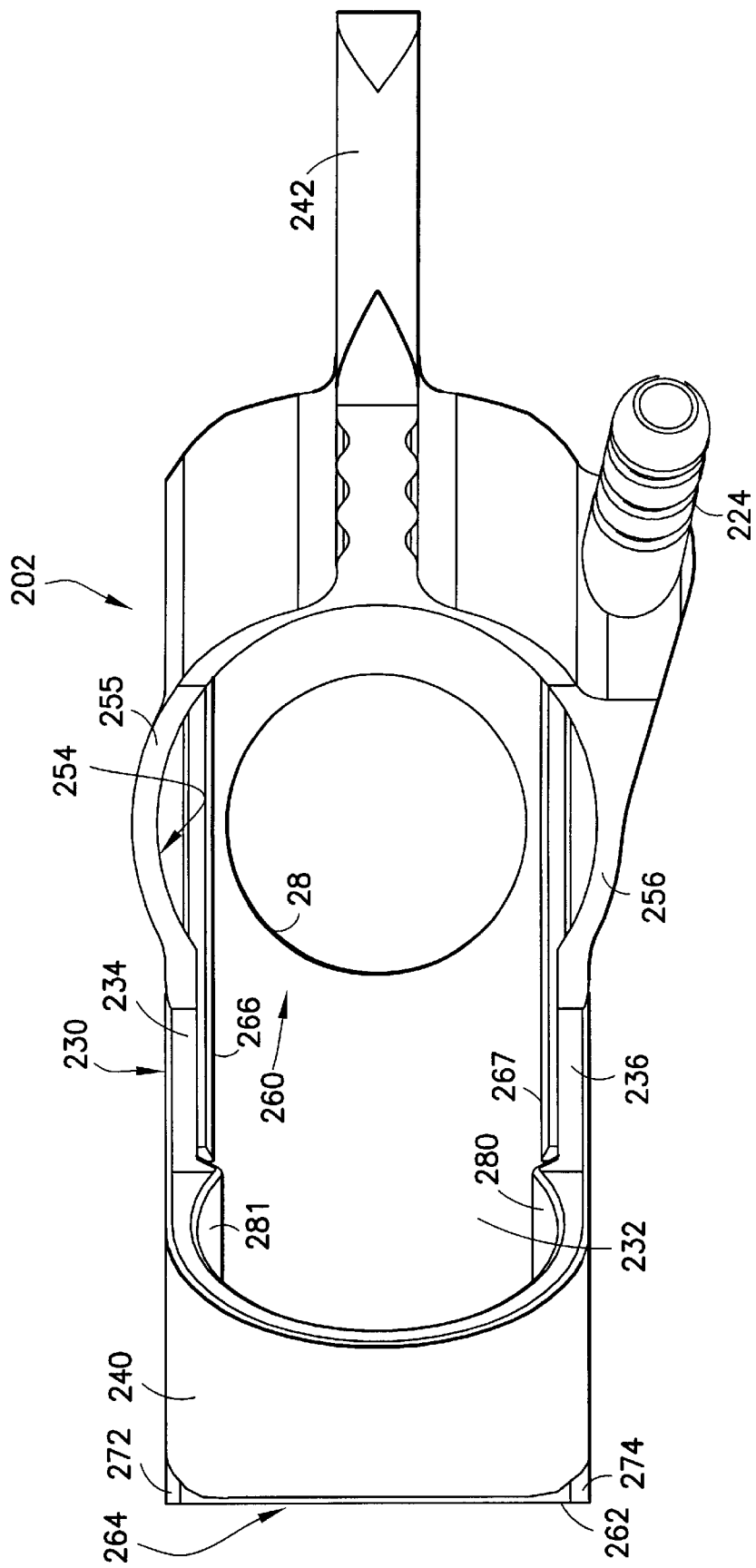
FIG. 19 is a top view of the suction ring of FIG. 18.

With reference to FIG. 17, an alternative cutting instrument 150 with a cutter head 151 according to the invention herein is illustrated. The cutter head 151 is characterized by a two-piece construction, including a base 152 and a cap 154. The base 152 and cap 154 together define a blade cavity 156 receiving blade assembly 56, including the blade 58 and blade holder 60. The base 152 provides the foot of the cutter head and extends upwardly to mount bearings 158 for drive shaft 90, including drive pin 92, extending from cooperating handle drive 18, not otherwise shown. The base includes the lower half 161 of mounting shank 160, partially surrounding drive shaft 90.

The cap 154 includes the upper half 162 of mounting shank 160, and is secured to the base 152, when the handle drive 18 is threaded into the mounting shank surrounding the upper and lower mounting shank portions and holding them together. The cap 154 also partially defines the blade cavity 156. The cap 154 mounts a pair of spaced, rounded guides 168, which are the guide bars for this embodiment and are received in the guide slot 68 of the blade assembly 56, for guiding the blade assembly in its reciprocal motion. Springs 170 bias the guides 168 into guide slot 68.

In this embodiment, the cap is removed from the base to insert the blade assembly, and the cutter head is then secured to the cutting instrument by attaching the handle drive 18, and thereby also introducing the drive pin 92 to the drive track on the rear of the blade assembly.

The cutter head 151 also includes a toe 171 with a transparent portion 172 for viewing the cornea. This feature is equally applicable to cutter head 16 described above.

Another keratome 200 according to the invention herein is illustrated in FIGS. 18–29. The keratome 200 generally comprises a suction ring 202, and a cutting instrument 204. An applanator 205 cooperates with the suction ring 202 prior to incising a cornea section.

The cutting instrument 204 has a cutter head 206 which is the same as cutter head 16 described above, except for the shape of the blade cavity 210 and blade holder 212, which will be discussed in more detail below. Other parts of the cutter head 206 correspond to the same parts of cutter head 16, and are given the same reference numerals in the drawings and discussion of keratome 200.

The cutting instrument 204 also includes a handle drive 218, which is similar in its internal structure to the handle drive 18 of keratome 10 described above. The handle drive 218 is distinguished by a tubular body 220 that is elongated with respect to the tubular body 100 of handle drive 18, the elongated tubular body extending between the cutter head 206 and an adjustable stop ring 222 surrounding the tubular body 220 adjacent flared collar 103. The drive shaft of the handle drive 218 is, of course, also elongated to provide drive pin 92 extending into the blade cavity 210, again as more fully described below.

Figure 20:
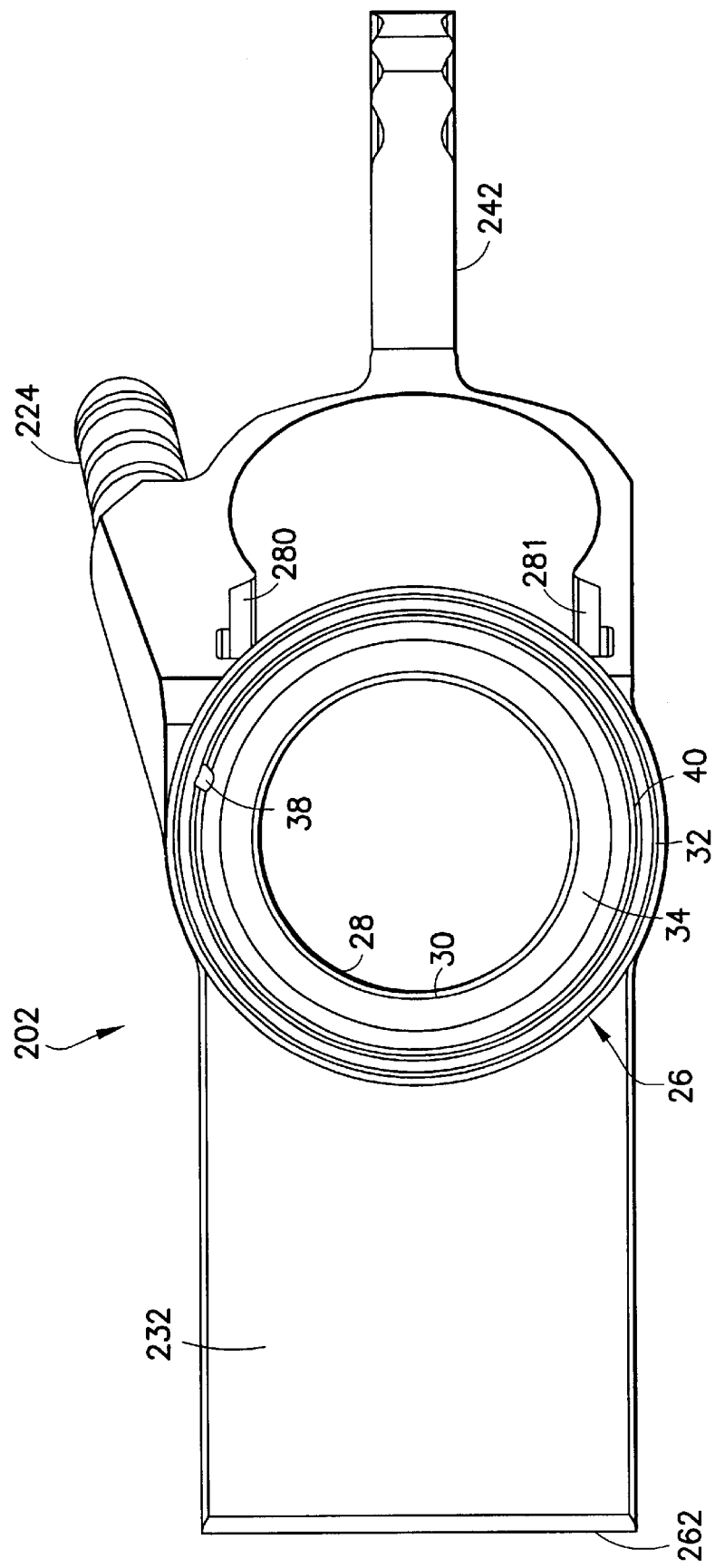
FIG. 20 is a bottom view of the suction ring of FIG. 18.
Figure 21:
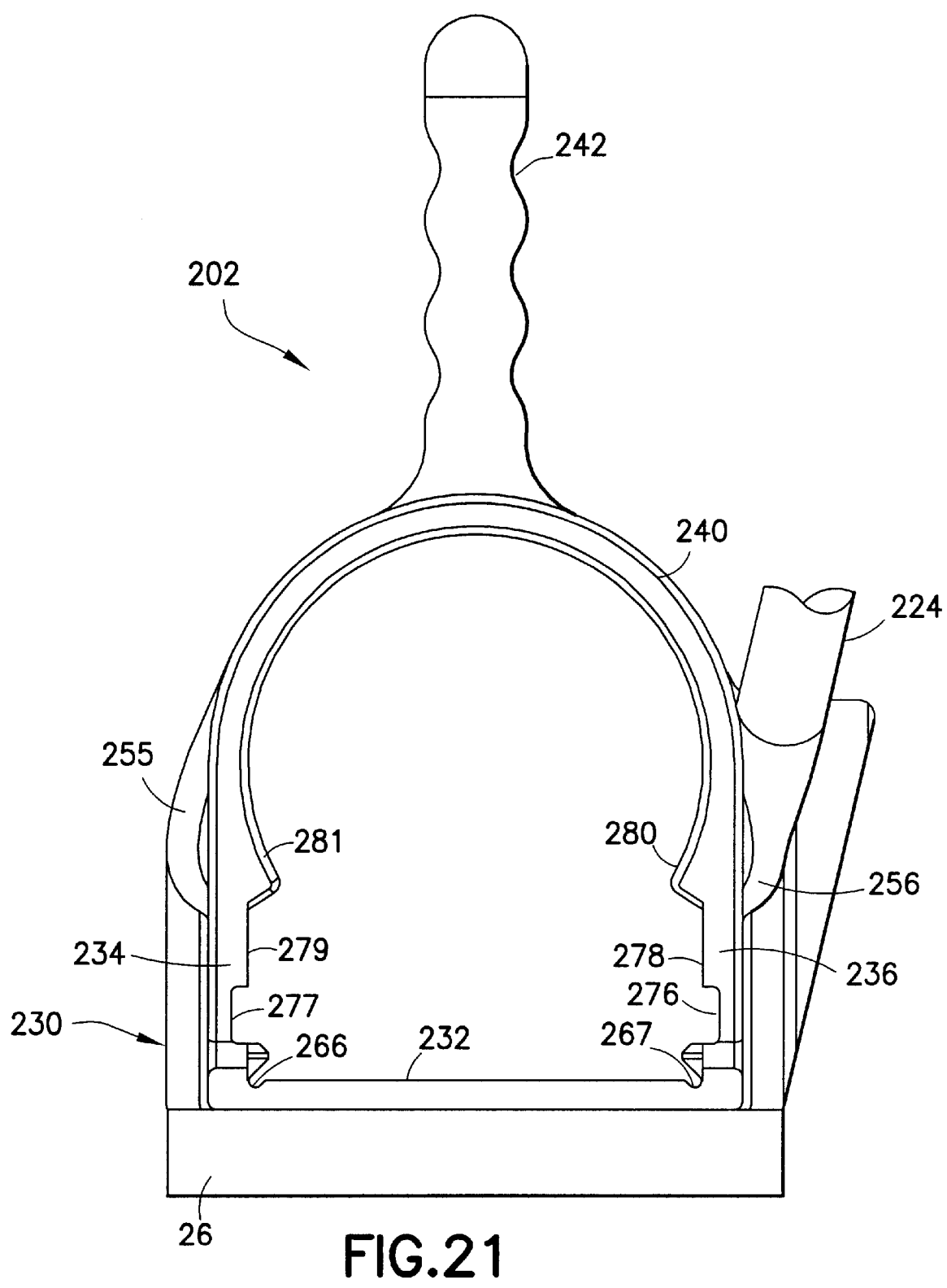
FIG. 21 is an end view of the suction ring of FIG. 18.

The suction ring 202 is shown in FIGS. 18–21, as well as in other figures in combination with other elements of the keratome 200. The suction ring 202 includes an eye ring 26, which is the same as the eye ring 26 described above in connection with suction ring 12. With particular reference to FIG. 20, the eye ring 26 has an inner annular contact surface 30 adjacent a cornea aperture 28, and an outer annular contact surface 32. A suction channel 34 is defined between the inner and outer contact surfaces 30, 32, and a secondary distribution channel 40 extends around the suction channel 34 and intersects with conduit stem opening 38. The suction ring is provided with a conduit stem 224 for connection with the source of negative pressure, such as shown in FIG. 8 and described above. The conduit stem is not shown in all of the figures for clarity of the remaining parts.

The suction ring 202 has a shoe 230 including a planer bottom wall 232 from which the eye ring 26 depends and which also defines the cornea aperture 28. The shoe 230 has side walls 234 and 236 upstanding from the bottom wall 232, and the side walls 234 and 236 merge with a guide hoop 240 at an entrance end of the suction ring 202 and with a handle 242 at the handle end of the suction ring 202.

The suction ring 202 cooperates with an applanator 205 in measuring the cornea segment 20 prior to incising thereof. The applanator 205 has a generally tubular barrel portion 244 and a handle portion 246, which are integrally fabricated of an optically clear material, such as Lexan®. The applanator has a measuring surface 248 which is recessed below the end 249 of barrel 244. The depth of recess is preferably the same height that the cutting edge 72 of the cutting blade 58 is disposed above the bottom wall 232 as the cutter head 206 is employed to incise the cornea. The measurement surface 248 is provided with a plurality of concentric rings 250 which are used in measuring the size of the cornea segment. In the embodiment shown, the inner ring is 8.5 millimeters in diameter, the central ring is 9.0 millimeters in diameter and the outside ring is 9.5 millimeters in diameter. The applanator is flattened at 252 for clearance with respect to the suction ring.

Figure 28:
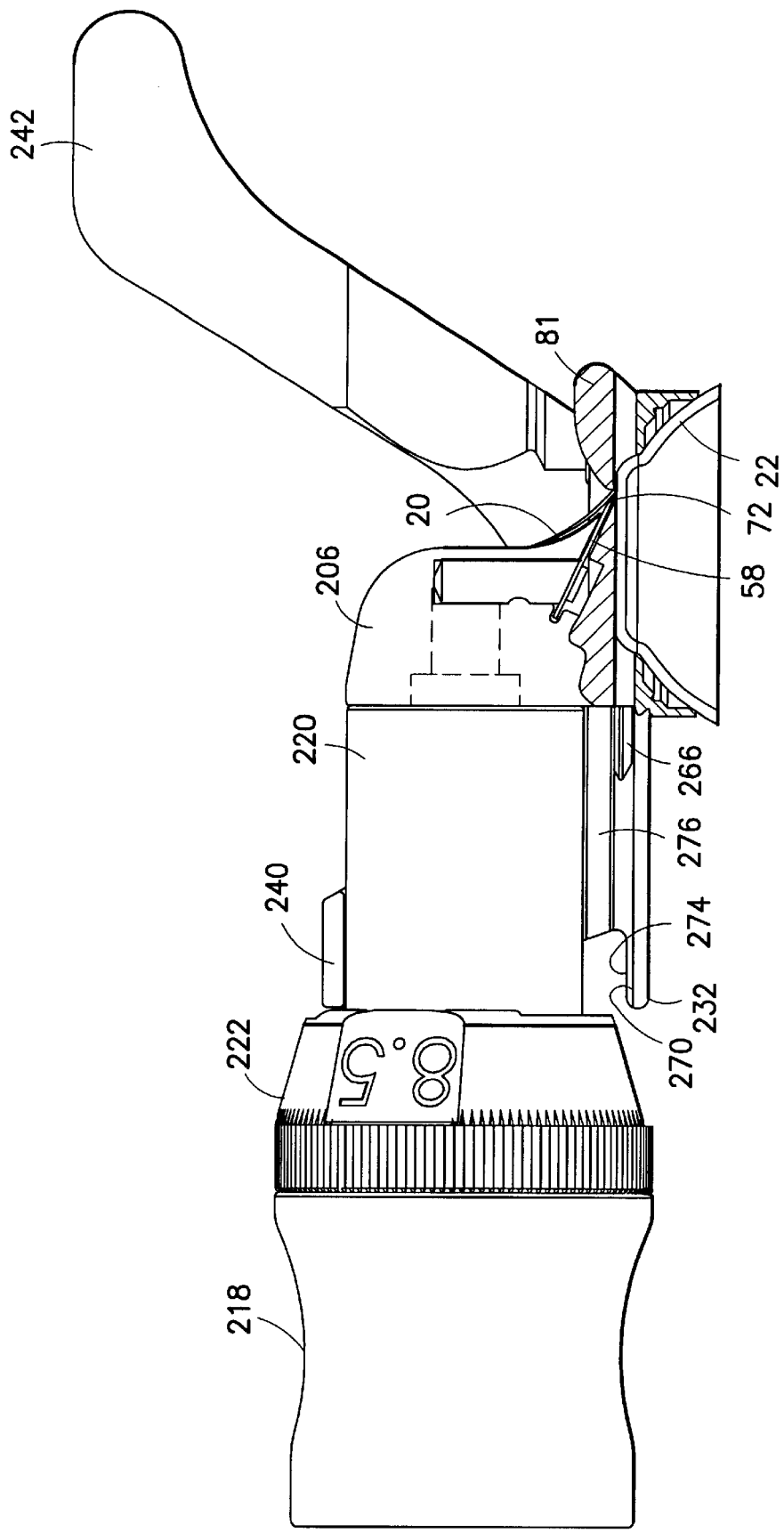
FIG. 28 is a side elevation view, partially in section, of the cutting instrument and suction ring of FIG. 22 in their stopped position.

The side walls 234 and 236 of the suction ring define opposed curved socket portions 255 and 256 of a socket 254, which positions the barrel 244 of the applanator 205 centrally over the cornea aperture 28, as seen in FIGS. 26 and 28. The flats 252 of the applanator accommodate portions of the side walls which define guideways for the cutter head 206, as more fully discussed below.

Figure 29:
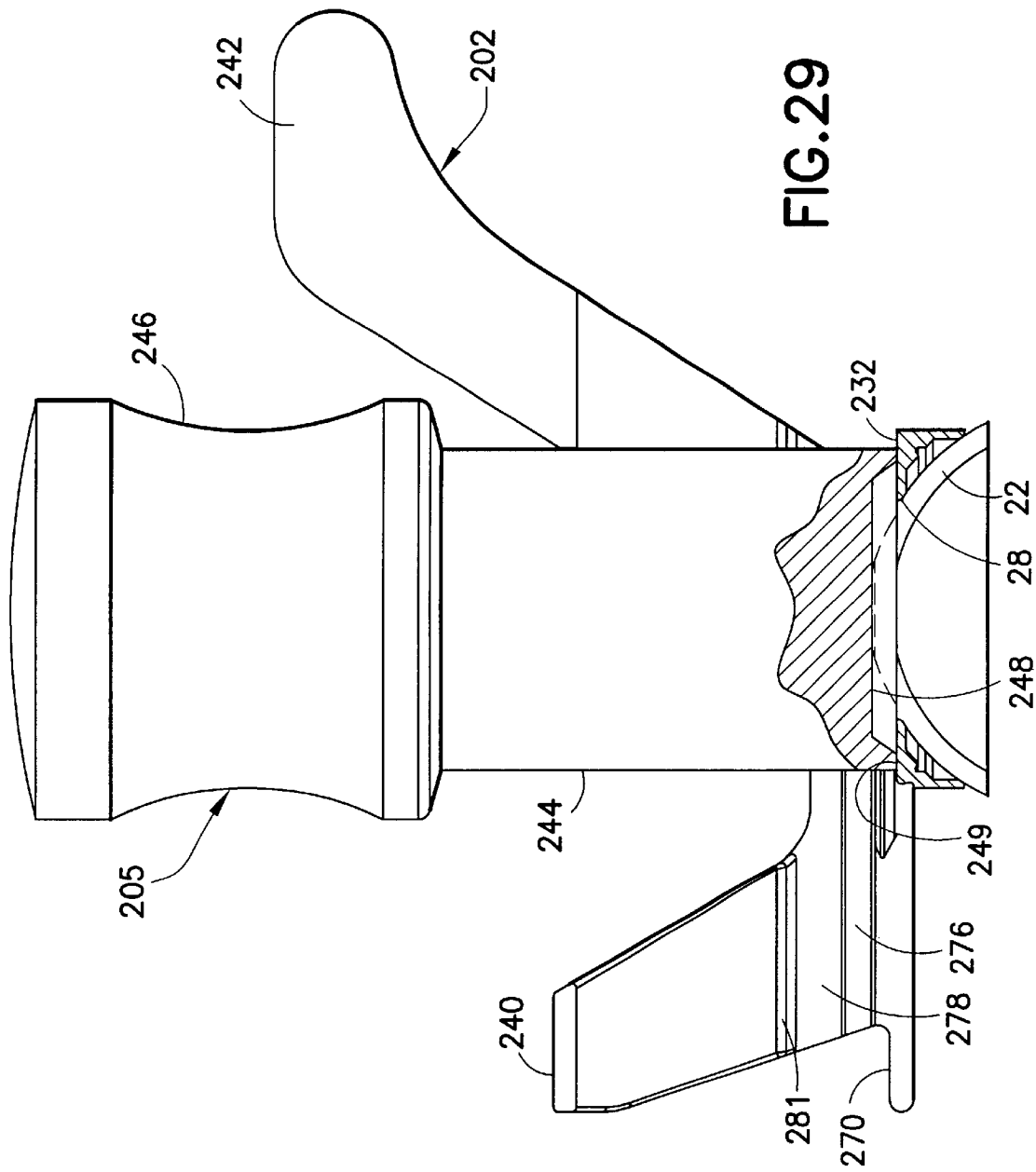
FIG. 29 is a side elevation view, partially in section, of the suction ring and applanator of FIG. 18.

As best seen in FIG. 29, when the suction ring 202 is secured to eye 24, the cornea 22 protrudes through the cornea aperture 28 and extends above the bottom wall 232. When the applanator 205 is received in the socket defined by the curved socket portions 254 and 256 of the suction ring side walls, and is also supported with its end 249 on the bottom wall 232, the cornea is in contact with the measuring surface 248 of the applanator. The surgeon views the concentric rings and cornea contact portion axially through the applanator 205. The diameter of the contact portion of the cornea is ascertained by reference to the concentric rings 250 on the measurement surface, and corresponds to the size of the cornea segment 20 which will be incised by the cutting instrument 204. Upon ascertaining the size of the cornea segment, the applanator is removed from the socket 254.

The keratome 200 is characterized by accurate engagement between the cutting instrument 204 and the suction ring 202, and by easy insertion of the cutting instrument into the suction ring. To this end, the shoe 230 of the suction ring defines a cutting guideway 260 configured for receiving the cutter head 206 in precision mating sliding engagement. Adjacent the precision cutting guideway 260 and extending to the entrance end 262 of the suction ring is an entrance guideway 264, with the guide hoop 240 providing transition between the entrance guideway 264 and the cutting guideway 260.

The cutting guideway 260 includes precision guide grooves 266 and 267 respectively at the intersections of the bottom wall 232 and sidewalls 234, 236. The guide grooves 266, 267 respectively slidingly receive the tongues 88 and 89 of the cutter head 206. The precision guide grooves 266 and 267 are fully defined only in the cutting guideway 260 and the entrance guideway 264 serves to position the cutter head 206 for accurately and easily engaging the tongues 88 and 89 in the precision guide grooves 266 and 267.

The entrance guideway 264 begins with an entrance ramp portion 270 of the bottom wall 232, the entrance ramp portion 270 being provided with curbs 272 and 274 at its marginal edges. The lower portions of guide grooves 266, 267 are partially defined adjacent the curbs 272, 274, such that the tongues 88, 89 can drop into the partially defined guide grooves; however, this does not require precision alignment and is merely part of the function of the entrance guideway 264 in orienting and positioning the cutter head with respect to the cutting guideway. At the entrance to the guide hoop 240, the side wall 236 defines a toe slot 276 and a toe slot ramp 278. The toe slot ramp 278 is positioned under a side rail 280 which extends inwardly from the toe slot ramp 278 and the interior of the guide hoop 240. The side wall 234 similarly defines toe slot 277, a toe slot ramp 279 and a side rail 281. The side rails 280 and 281 are discontinuous at the socket walls 255 and 256 as are the toe slot ramps 278 and 279.

Figure 22:
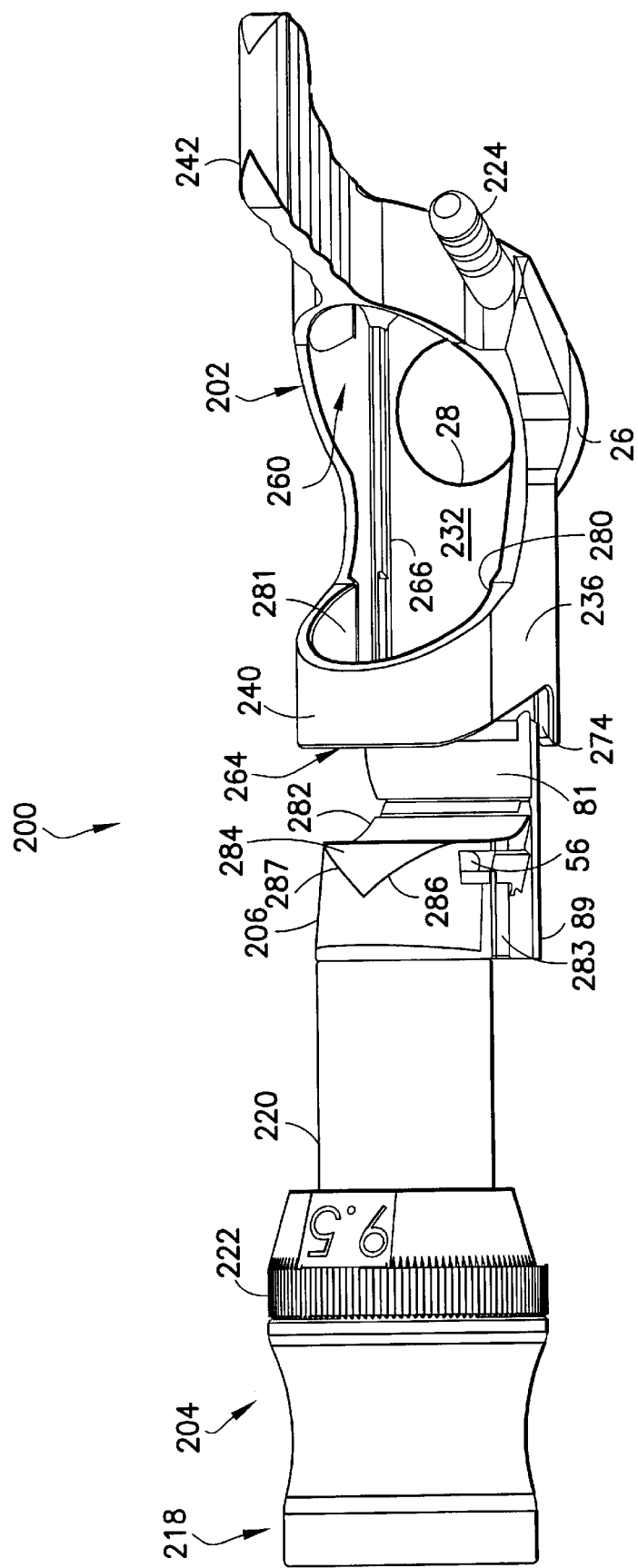
FIG. 22 is a perspective view of the cutting instrument and suction ring of the keratome of FIG. 18.
Figure 23:
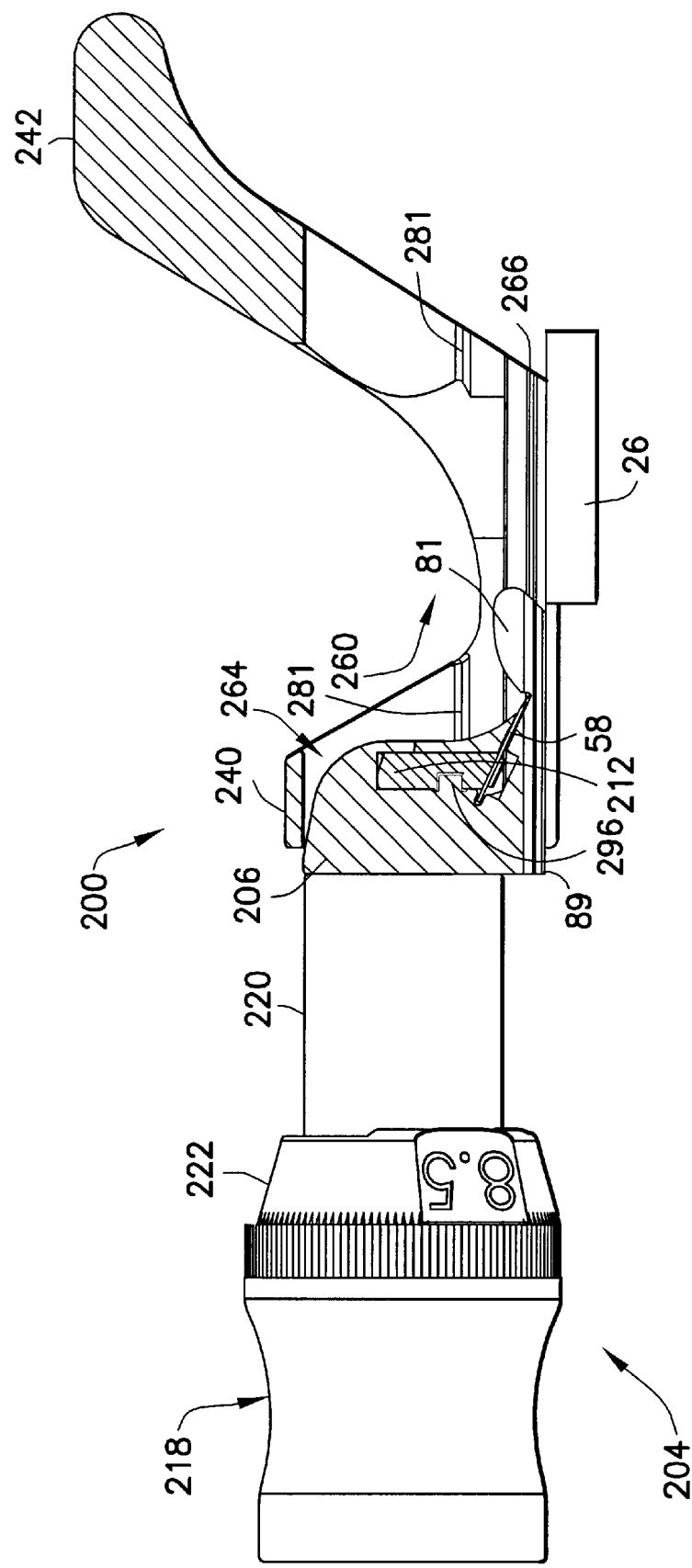
FIG. 23 is a side elevation view, partially in section, of the cutting instrument and suction ring of FIG. 22.

FIGS. 22 and 23 illustrate entry of the cutting instrument 204 into the suction ring 202. Although the user's hands are not shown, it will be appreciated that the user will hold the handle 242 in one hand and will manipulate the cutting instrument 204 with the other hand. It is advantageous to have both hands involved in the insertion of the cutting instrument 204 into the suction ring 202, in that the user can stabilize the suction ring 202 on the eye by sensing and compensating for any insertion forces, and also because the use of two hands tends to achieve better spacial orientation and physical coordination in making the insertion.

The toe 81 of the cutter head 206, including the leading portions of tongues 88 and 89, are placed against the entrance ramp portion 270 of the shoe 230. If the tongues 88 and 89 are placed between the curbs 272 and 274, the toe is guided along bottom wall 232 into the guide hoop 240, and the tongues then enter the fully defined guide grooves 266 and 267. If the tubular body 220 and cutter head 206 of the cutting instrument 204 are not axially oriented with respect to the cutting guideway 260, a curved forehead 284 or one of flanking edges 286 and 287 defining the outer edges of the forehead 284 engages the guide hoop 240 and directs the cutting instrument 204 toward alignment. This engagement and continued forward movement of the cutting instrument 204 into entrance guideway 264 causes the tubular body 220 and cutter head 206 to be axially aligned with the cutting guideway 260, and permits the tongues 88, 89 to enter the guide grooves 266 and 267, as seen in FIG. 23.

If the toe 81 of cutter head 206 is somewhat tilted or initially misaligned, it will contact one of the toe slots 276, 277, or one of the toe slot ramps 278, 279, which will direct the toe into an adjacent respective toe slot. This provides an initial near alignment which is further corrected into axial alignment by contact of the forehead 284 or the transition edges 286 and 287 with the guide hoop 240, ultimately resulting in axially alignment of the cutting instrument 204 with the cutting guideway, and engagement of the tongues 88, 89 in the precision guide grooves 266, 267.

In all instances in which the toe 81 is inserted into the entrance guideway with the toe positioned under the side rails 280 and 281, the entrance guideway will is accept the toe and by contact with the forehead 284 and transition edges 286, 287 the remainder of the cutter head will achieve alignment of the cutting instrument 204 for entry into the cutting guideway 260. It will be appreciated that the entrance guideway 264 tolerates misalignment on initial insertion and corrects the alignment as insertion into the entrance guideway 264 proceeds, making it extremely easy for the user to achieve the correct alignment of the cutting instrument 204 on the suction ring 202. The entrance guideway 264 has the additional benefit of providing entry to the suction ring 202 in an area spaced apart from the cornea aperture 28, thereby also preventing accidental damage to the cornea as a result of mis-engagement between the cutting instrument 204 and suction ring 202.

It will be noted that the cutter head 206 defines elongated side rail pockets 282 and 283 spaced upwardly from and parallel to the tongues 88, 89, and these pockets are matingly shaped with and slidingly the side rails 280, 281 of the suction ring 202. The diameter of the tubular body 220 is preferably selected so that it substantially matches the interior of the guide hoop 240, including the upper portions of the side rails 280 and 281, so that the cutter head 206 and tubular body 220 are slidingly accommodated in the guide hoop 240.

As the cutting instrument enters the cutting guideway 260, the tongues 88 and 89 are received in the precision grooves 266, 267, the side rails 280, 281 are received in the rail pockets 282, 283. As the cutting instrument progresses within the cutting guideway 260, the tubular body 220 is received in the guide hoop 240. Thus, the cutting instrument is fully supported and precisely positioned on the suction ring 202 as the cutting blade moves across the cornea aperture 28, as best seen in FIG. 28.

Figure 24:
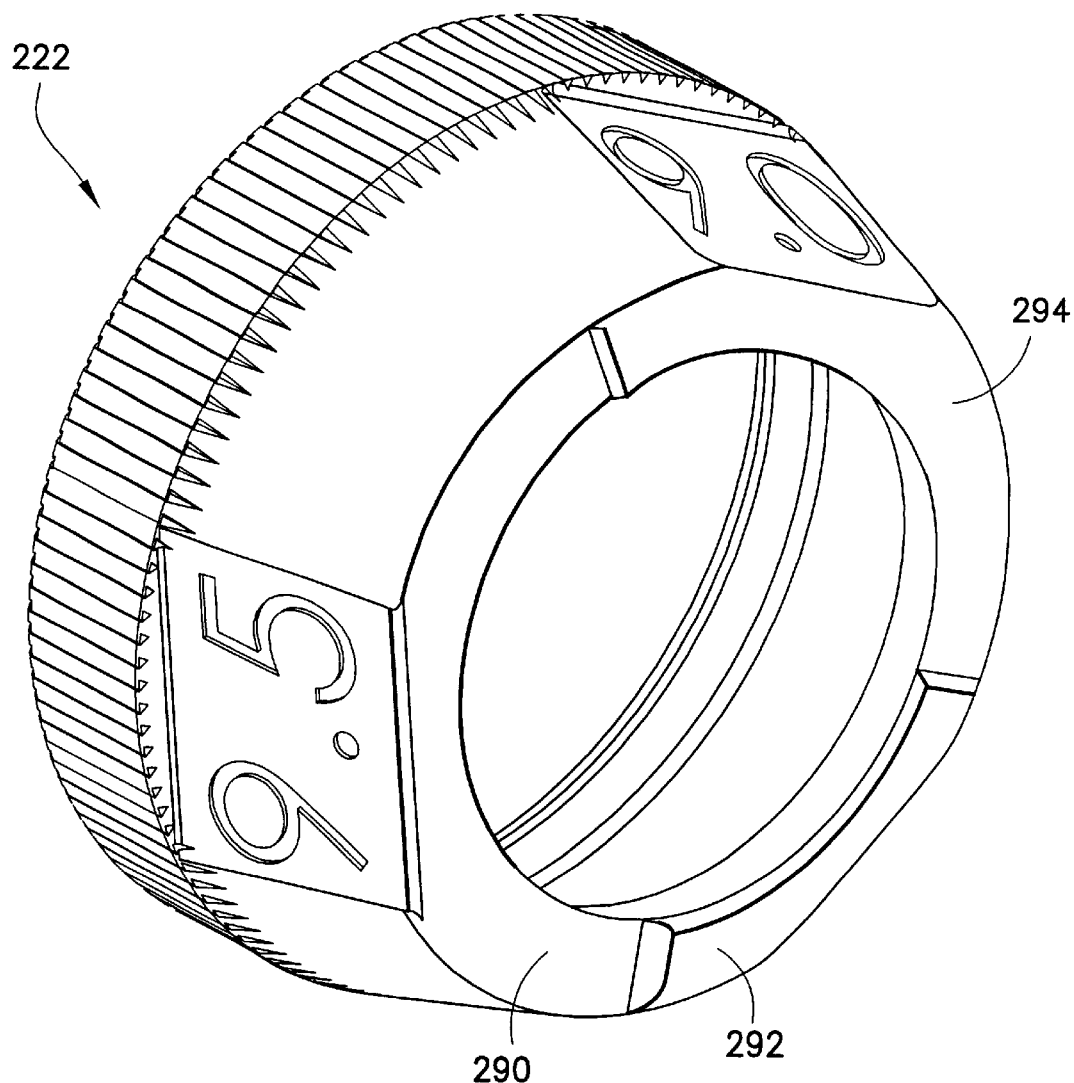
FIG. 24 is a perspective view of an adjustment collar for the cutting instrument of FIG. 22.

As also best seen in FIG. 28, before the cutting edge 72 of the cutting blade 58 moves completely across the cornea aperture, the stop ring 222 engages the guide hoop 240, limiting further insertion movement of the cutting instrument 204 and thereby preserving a hinge between an incised cornea section and the cornea. With particular reference to FIGS. 22, 24 and 28, the stop ring 222 has three stop surfaces 290, 292 and 294, which are marked with indicia coordinating the stop surfaces with the size of the cornea contact patch measured with the applanator 205. The user selects the desired stop surface corresponding to the measured size prior to inserting the cutting instrument 204 into the suction ring 202, and the stop ring contacts the guide hoop at 289 when the cut has proceeded for the desired, selected distance.

Figure 25:
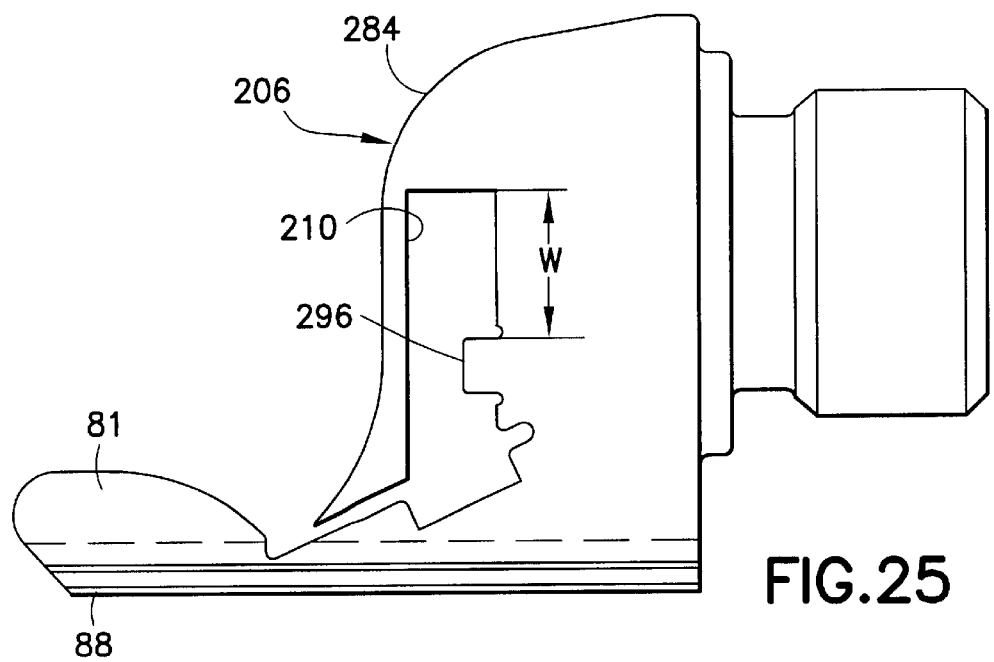
FIG. 25 is a side elevation view of the cutter head of the cutting instrument of FIG. 22.
Figure 27:
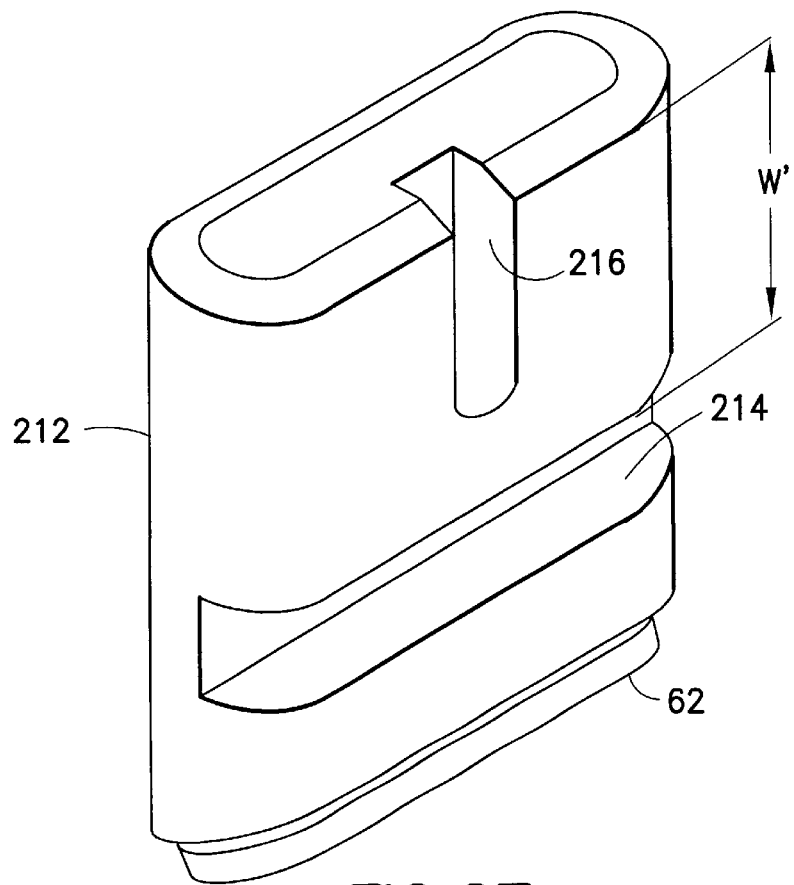
FIG. 27 is a perspective view of a blade holder of the cutting instrument of FIG. 22.

The keratome 200 is also characterized by stabilized reciprocating movement of the cutting edge 72 of blade 58, in order to achieve a very smooth incision of the cornea. With particular reference to FIGS. 25 and 27, the cutter head 206 defines a guide bar 296, which is substantially rectangular when viewed in side elevation. The blade holder 212 is provided with a mating rectangular guide slot 214, which receives and closely embraces the guide bar 296. In the embodiment shown, the blade holder 212 is fabricated of nylon and has a width W' from the guide slot to the top is larger than the corresponding width W from the guide bar to the top of the blade holder cavity by approximately 0.0005–0010 inches. This provides a "preloaded" engagement of the blade holder of the guide bar and achieves a positive, supported, stabilized alignment of the blade holder on the guide bar during reciprocating movement. The surface of the blade cavity is preferably coated with a nickel/Teflon® material to provide smooth reciprocation, effectively lubricating the preloaded interface between the guide bar 296 and the guide slot 214. Because the guide slot 214 is substantially larger and deeper than the guide slots on the blade holders of the previous embodiments, it is placed lower on the blade holder so that it does not intersect the drive track 216, which receives the eccentric drive pin 92 for reciprocating the blade holder 212. It should also be noted that the blade holder 212 may define a guide bar and the blade cavity define a guide slot, if desired. The blade 58 is secured to mounting stud 62 of the blade holder 212, and does not contact the cutter head 206.

Thus, the keratome 200 is used by first engaging the suction ring 202 with the patient's eye and then using the applanator 205 to measure the proposed cornea section. Stop ring 222 of the cutting instrument is set to the desired size, and the cutting instrument is inserted into the entrance guideway 264 of the suction ring. Engineered interference between the cutting instrument and the suction ring causes alignment with and entry into the cutting guideway 260 of the suction ring. The cutting guideway precisely positions the cutting blade as it incises the cornea. The cutting blade is reciprocated in making the cut, and the cutting blade is suspended with respect to contact with surrounding structure of the cutting instrument, and is stabilized for a smooth cut.

Another keratome 300 according to the invention provides automated reciprocal drive of a cutting instrument having a cutter head. With reference to FIGS. 30–46, as well as other Figures, the keratome 300 generally comprises an automated drive unit 310, a suction ring 312 and a cutting instrument 314 including a cutter head 330.

The cutting instrument 314, cutter head 330 and suction ring 312 are all similar to the cutting instrument 204, cutter head 206 and suction ring 202 of keratome 200 described above. However, the automated drive unit 310 of keratome 300 engages with the suction ring 12 and provides for automated translational movement of the cutter head 330 across the cornea of an eye.

Figure 30:
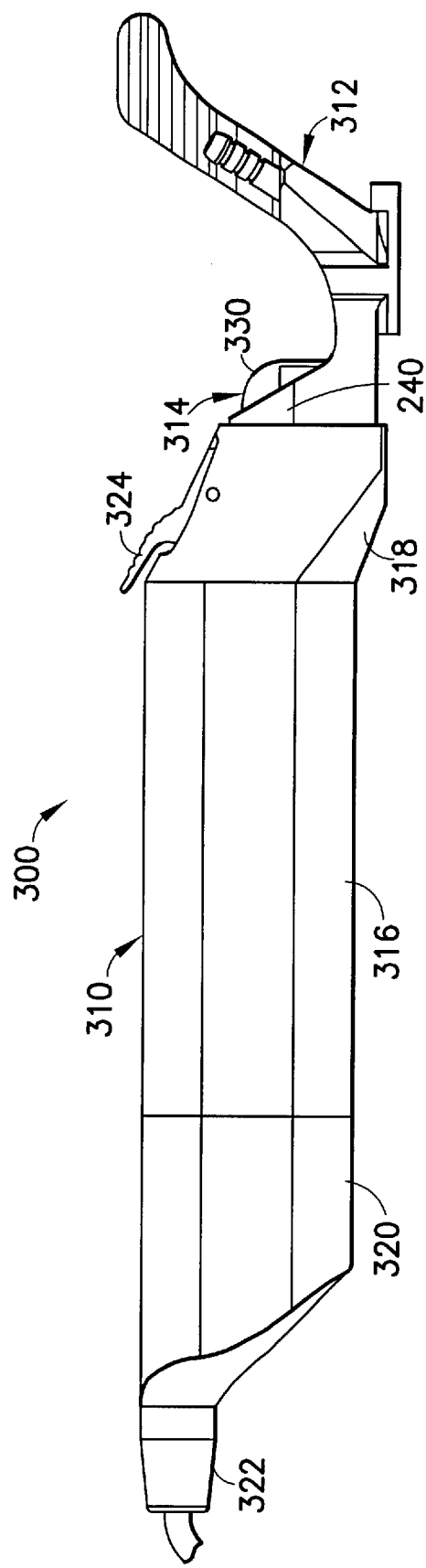
FIG. 30 is a side elevation view of another keratome according to the invention herein.
Figure 31:
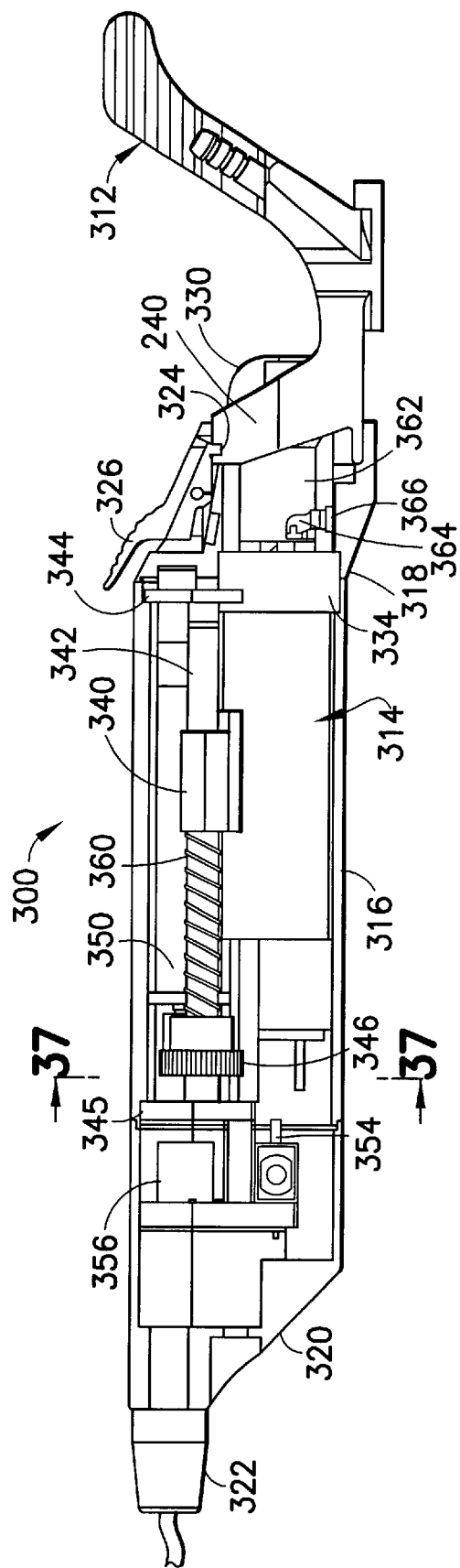
FIG. 31 is a perspective view of the keratome of FIG. 30, partially cut away.
Figure 32:
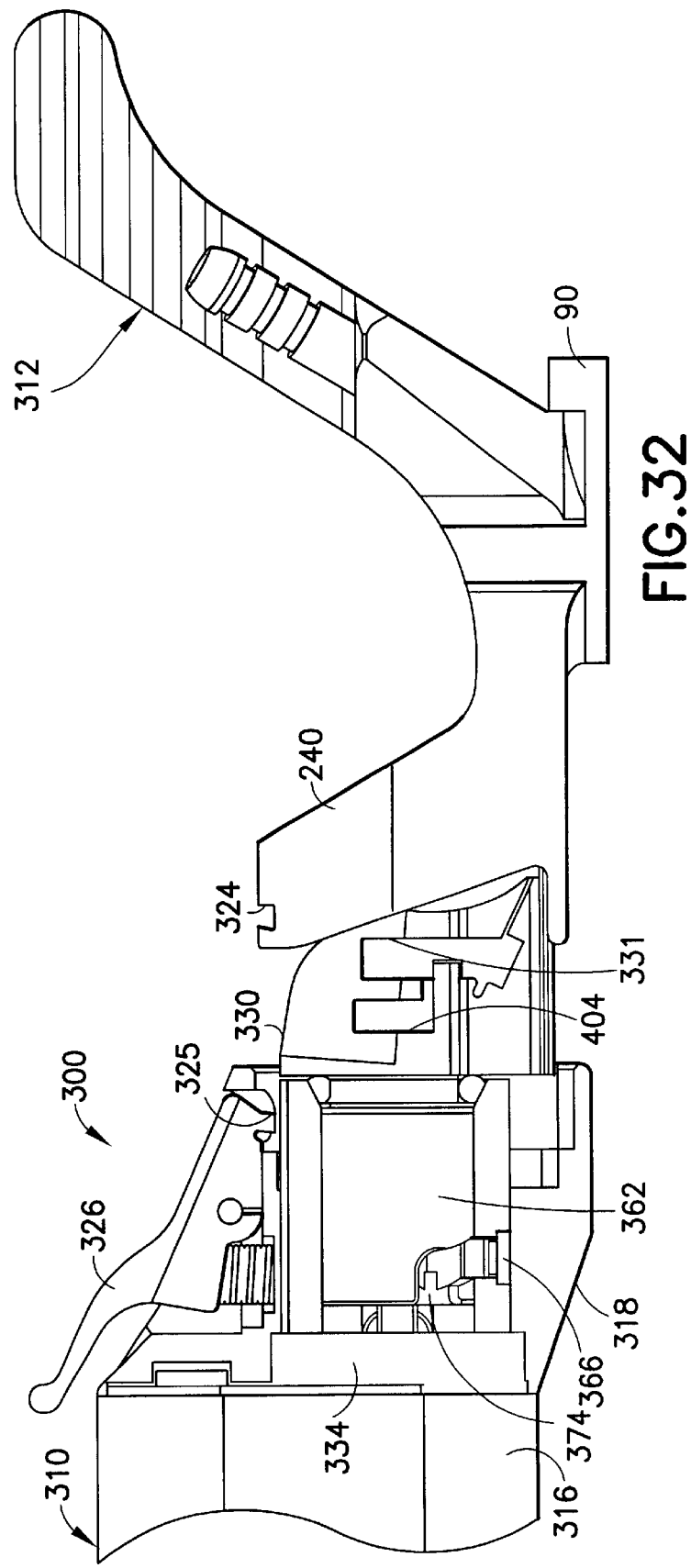
FIG. 32 is an enlarged sectional view of the cutter head entering the suction ring of the keratome of FIG. 30.

With reference to FIG. 30, the keratome 300 first comprises automated drive unit 310, having a main housing 316, a front transition housing 318, and a rear transition housing 320 terminating in a cable cap 322 from which the wires necessary to power the keratome extend. The front transition housing 318 is designed to engage with guide hoop 240 of the suction ring 312 and, as seen in FIGS. 31 and 32, the suction ring 312 defines a notch 324 receiving tongue 325 of a pivotal latch 326 of the front transition housing 318.

Figure 33:
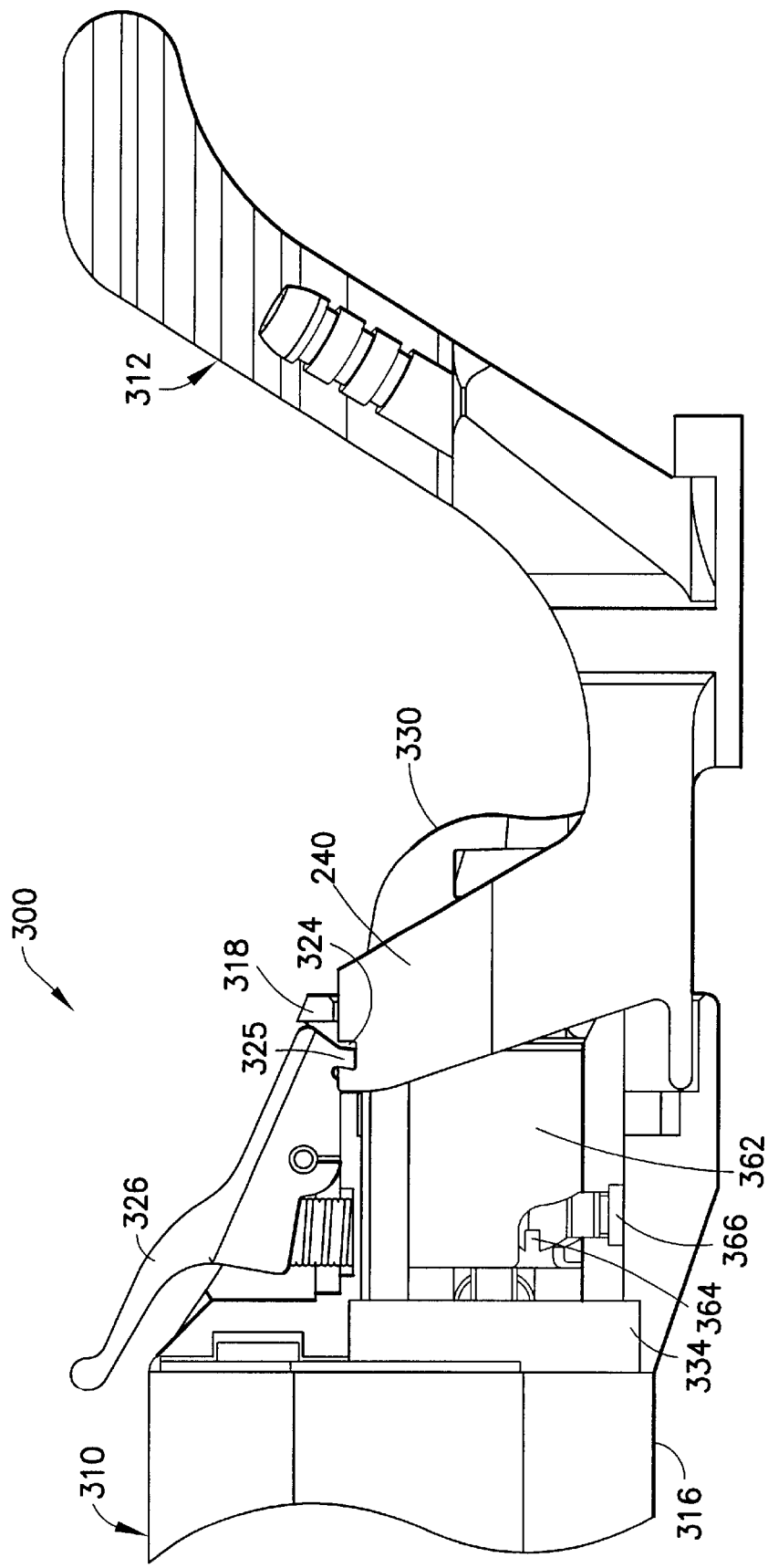
FIG. 33 is an enlarged, partially sectional view of the cutter head and automated drive unit engaged with the suction ring of the keratome of FIG. 30.
Figure 34:
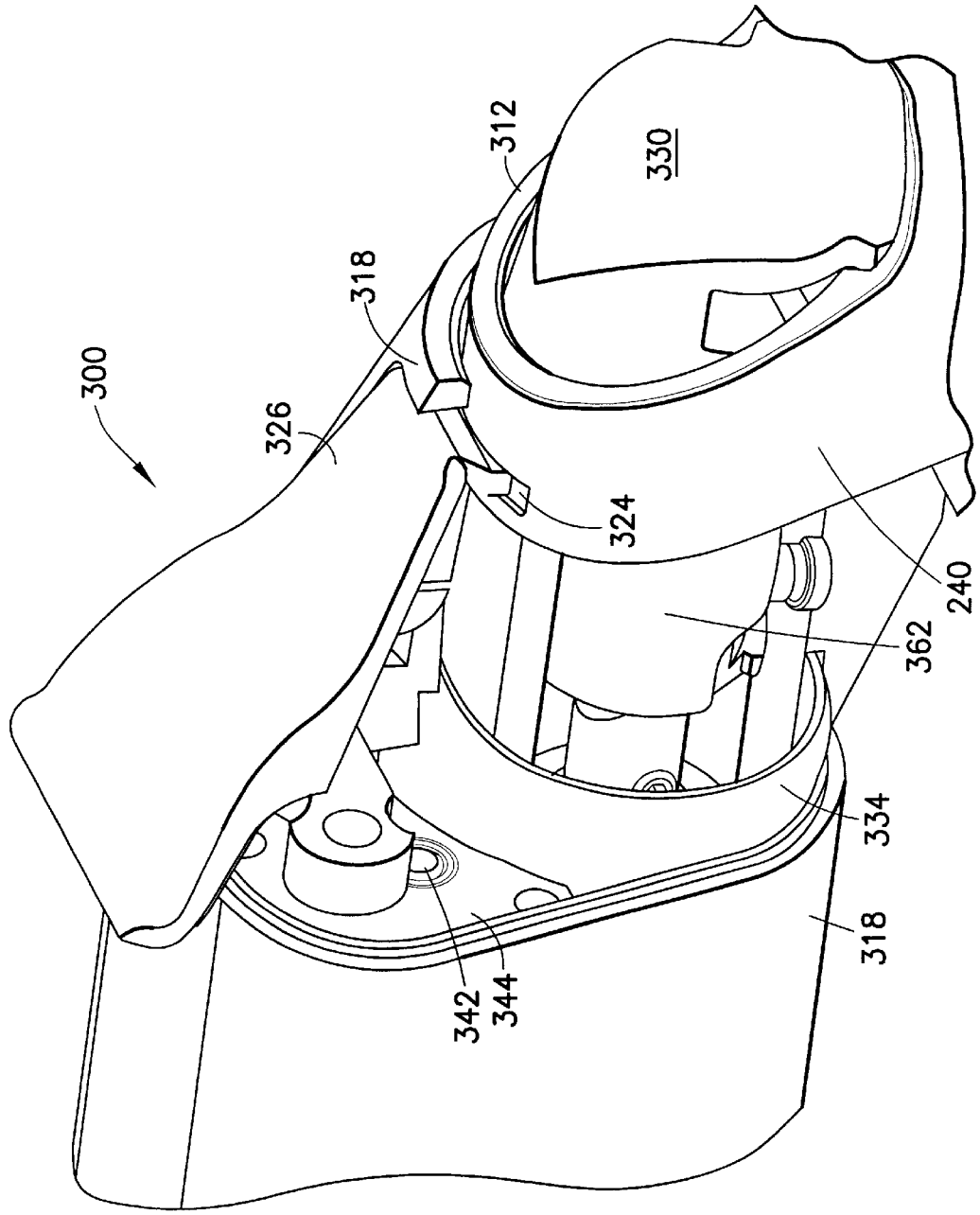
FIG. 34 is a perspective view of a portion of the keratome of FIG. 30, showing the cutter head and automated drive unit engaged with the suction ring.
Figure 35:
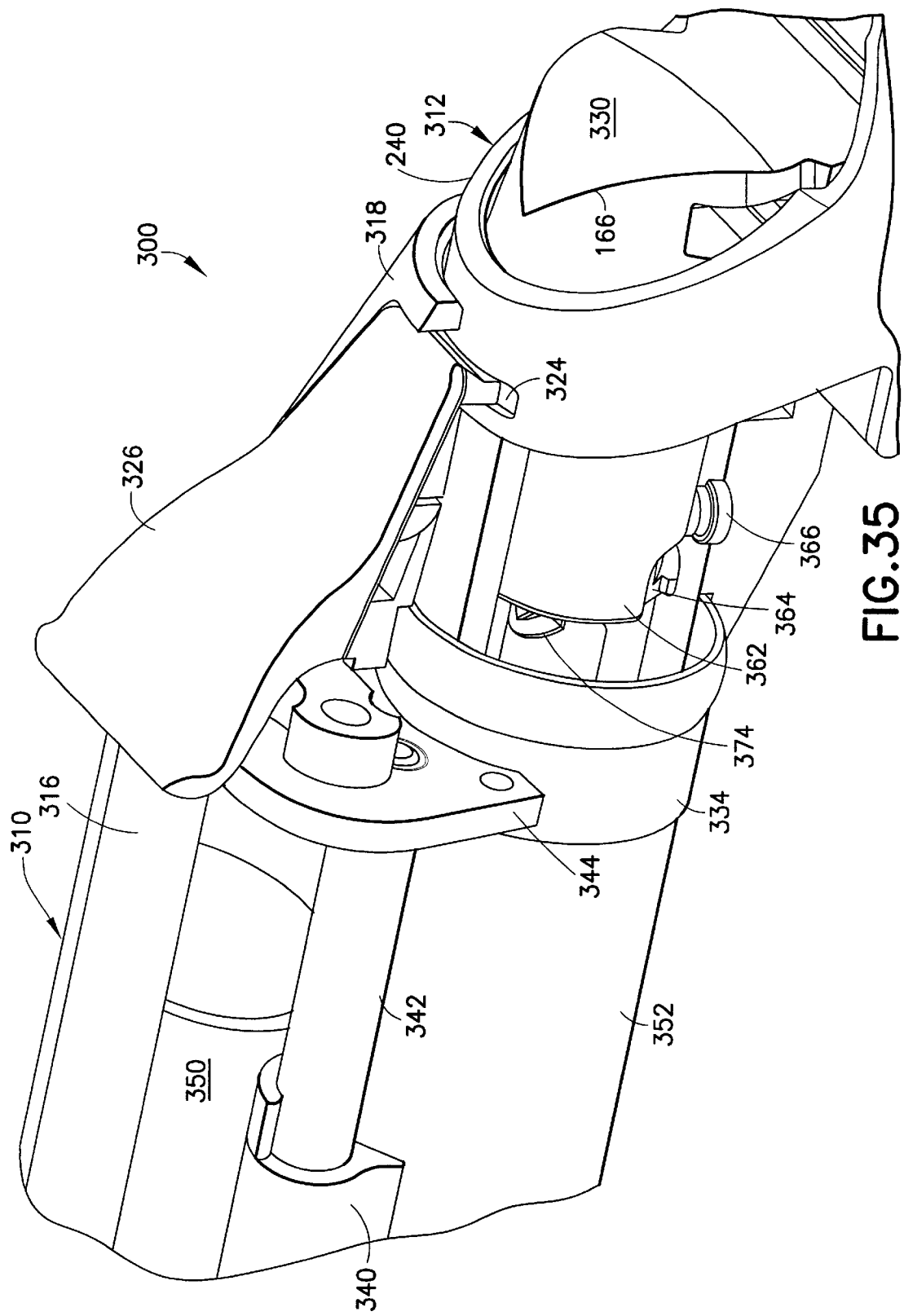
FIG. 35 is a perspective view a portion of the keratome of FIG. 30, similar to the view of FIG. 34 and additionally cut away.
Figure 36:
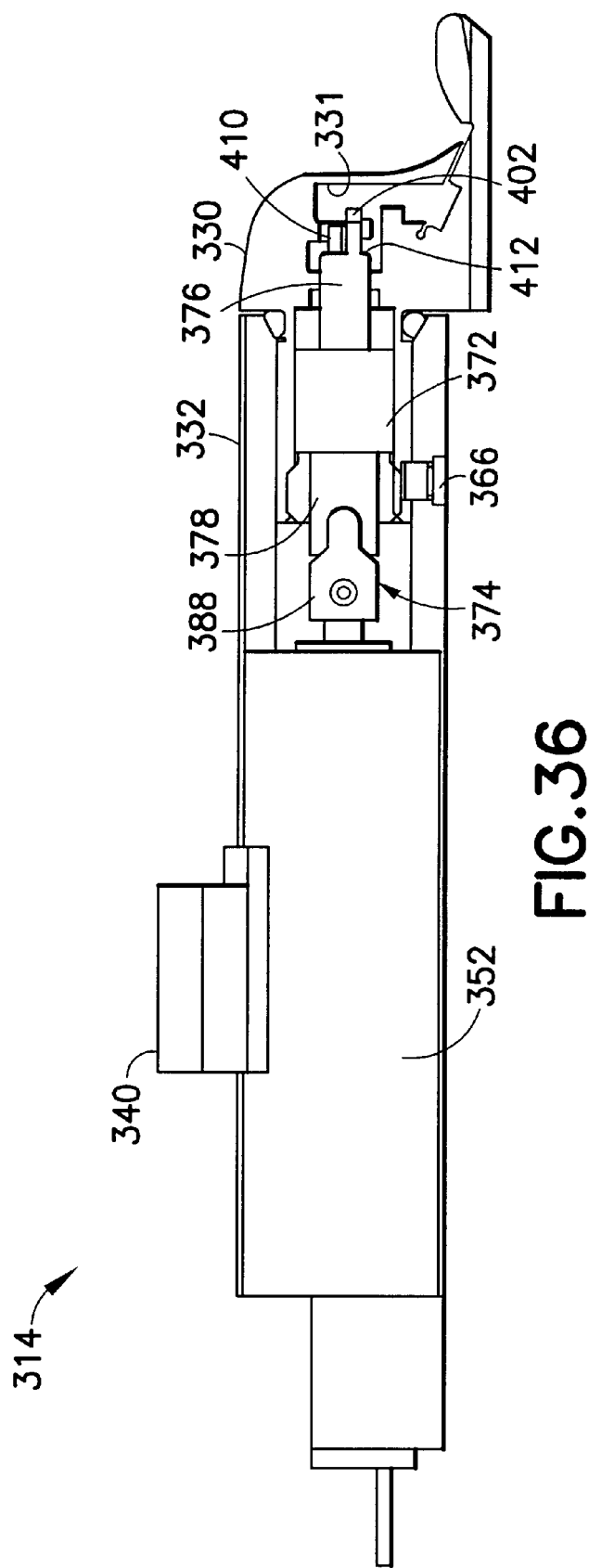
FIG. 36 is side elevation view, partially cut away, of the cutting instrument component of the keratome of FIG. 30.

The cutting instrument 314 includes a cutter head 330, which is similar to cutter head 206 described above. With reference to FIG. 36, the cutting instrument 314 defines a generally tubular body 332, and with reference to FIGS. 31–35, the tubular body is guided for reciprocal motion in the automated drive unit 310 by a bushing 334 at the front of the automated drive unit. The cutter head 330 is guided into the suction ring 312 in the manner discussed above with respect to cutter head 206 and suction ring 202 and as shown in FIG. 32. With reference to FIG. 33, when the cutter head 330 has entered the guide hoop 240, the front transition housing 318 also receives and engages with the rear portion of the suction ring and the tongue 325 of latch 326 is received in notch 324 to secure the automated drive unit 310 and cutter instrument 314 to the suction ring 312. The suction ring is, of course, secured to an eye in performing a cornea incision.

Figure 37:
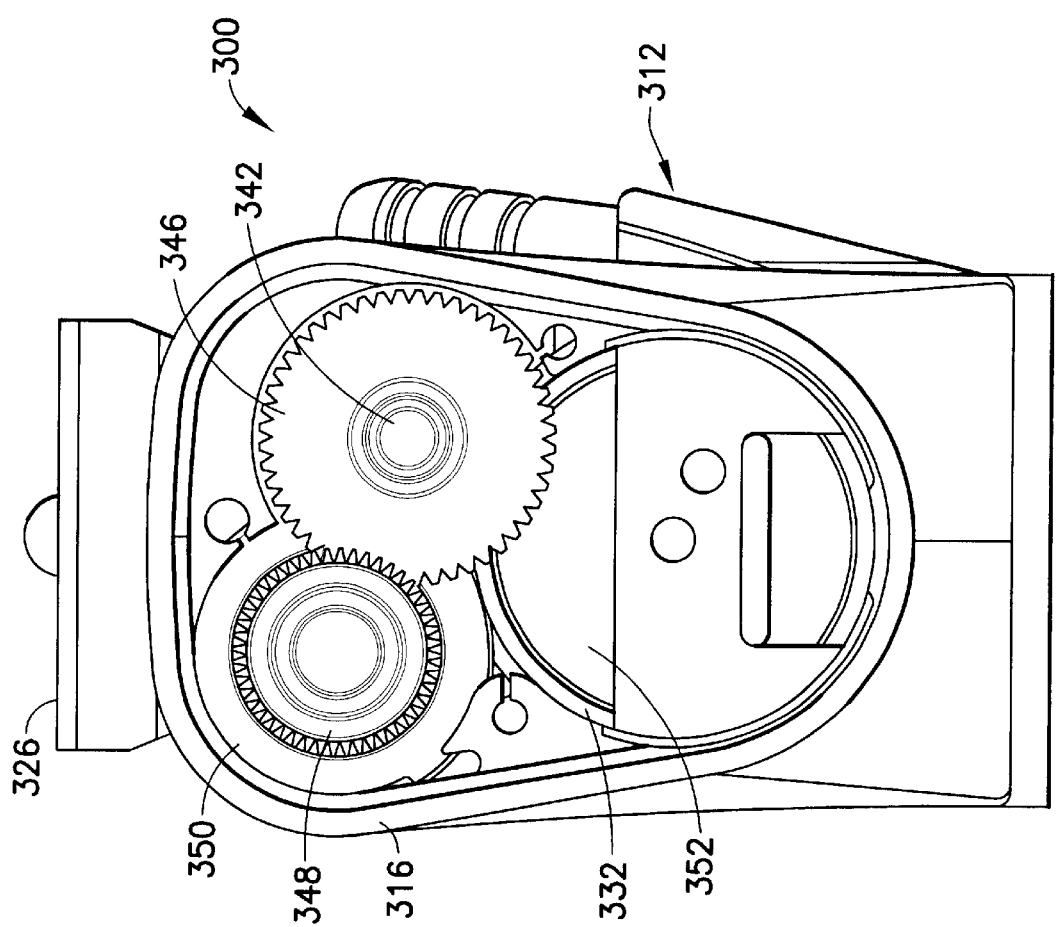
FIG. 37 is a sectional view of the keratome of FIG. 30, taken along the lines 37—37 of FIG. 31.
Figure 38:
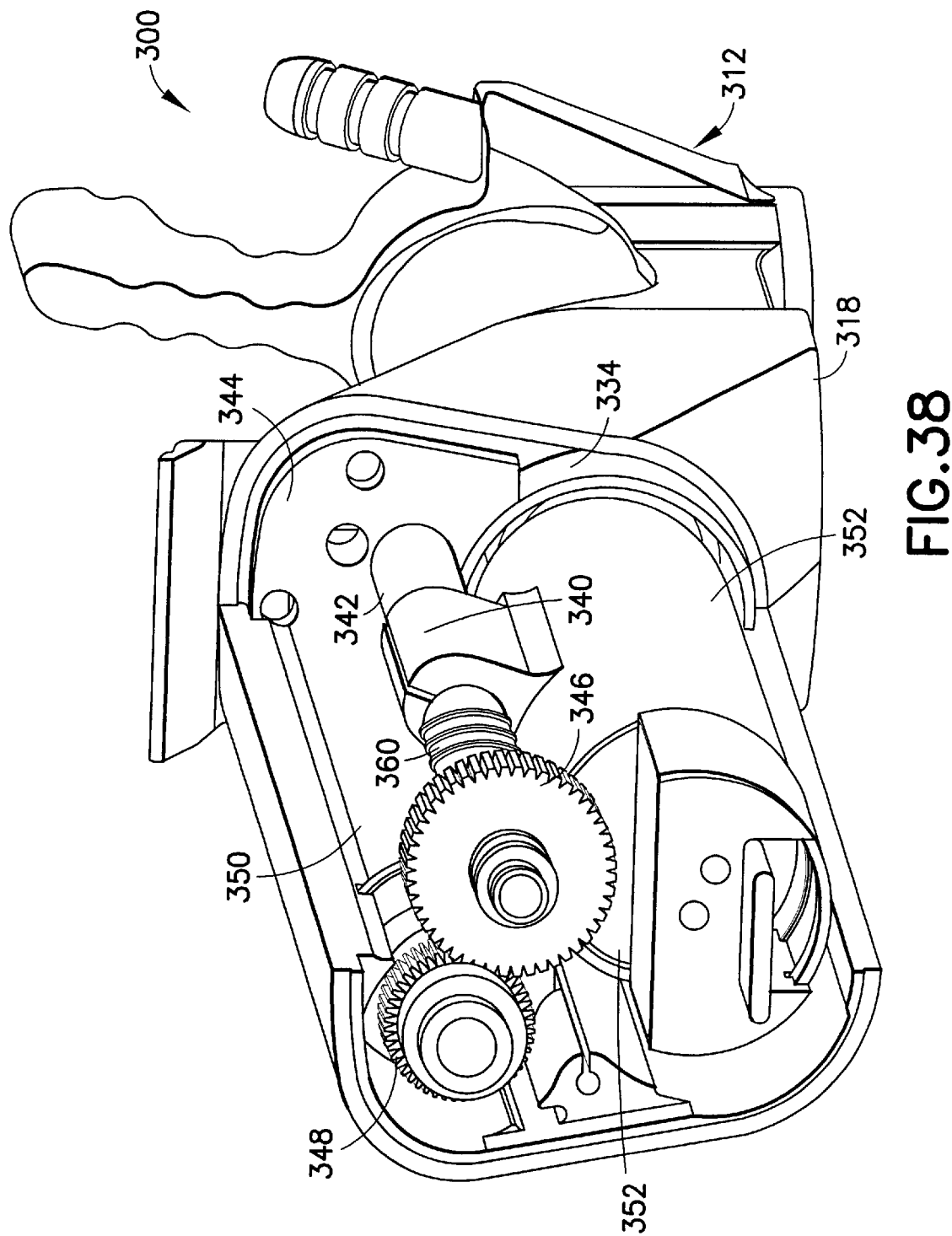
FIG. 38 is a foreshortened perspective view, partially cut away, of the keratome of FIG. 30.
Figure 39:
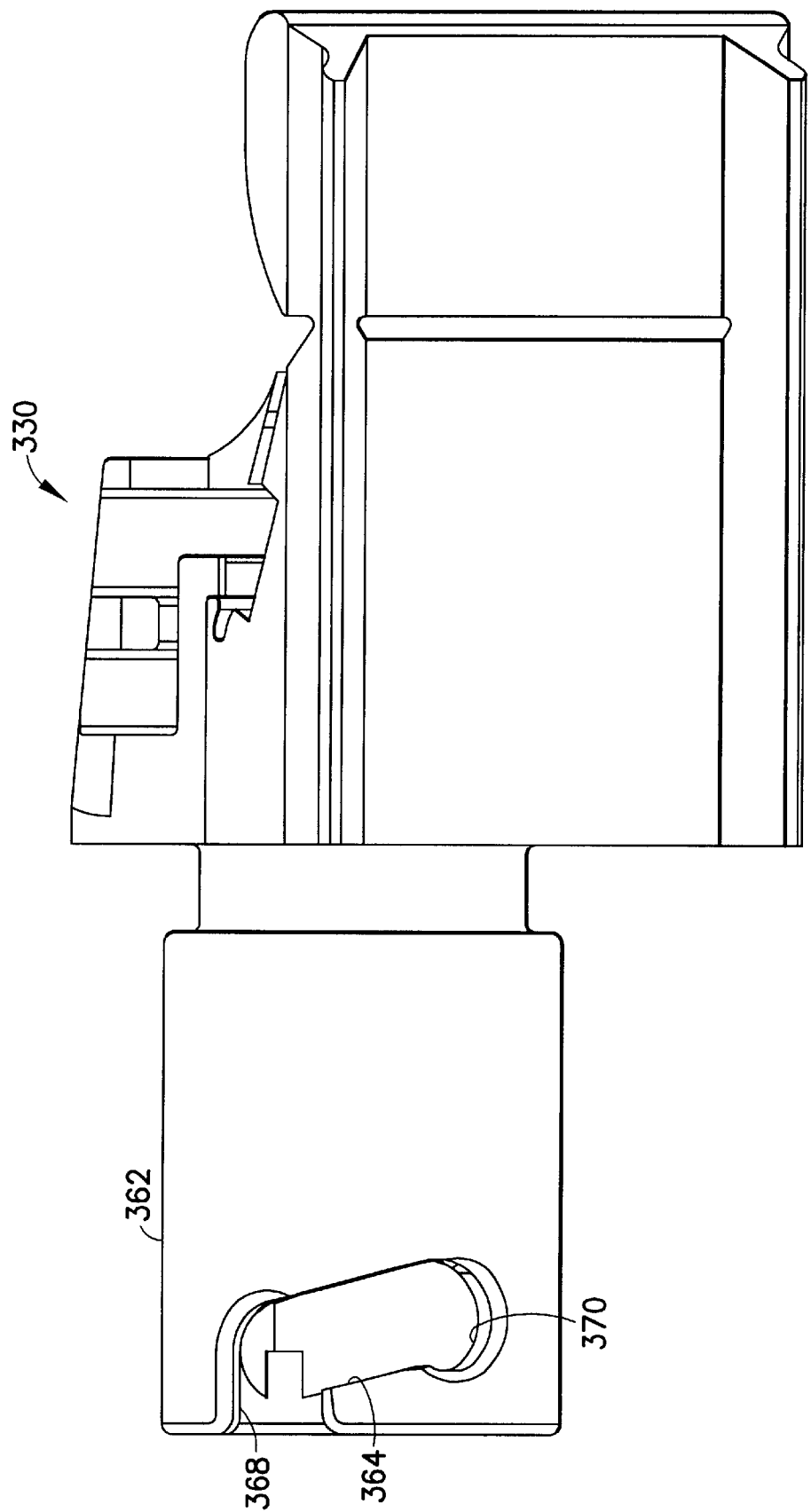
FIG. 39 is a perspective view toward the bottom of the cutter head of the keratome of FIG. 30, illustrating its mounting shank configuration.
Figure 40:
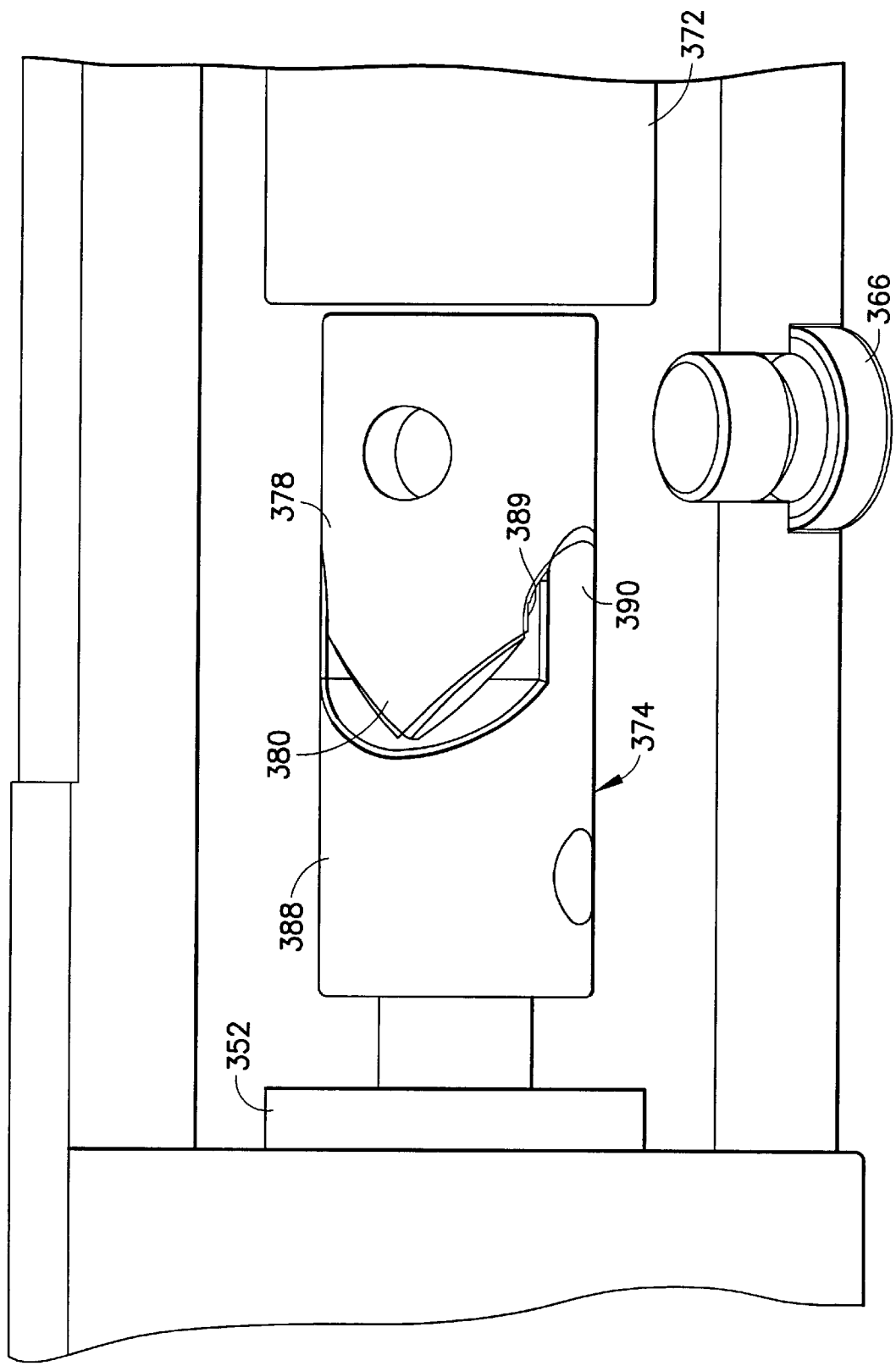
FIG. 40 is an enlarged view of the coupling between the cutter head drive shaft and the motor drive of the cutting instrument of the keratome of FIG. 30.
Figure 41:
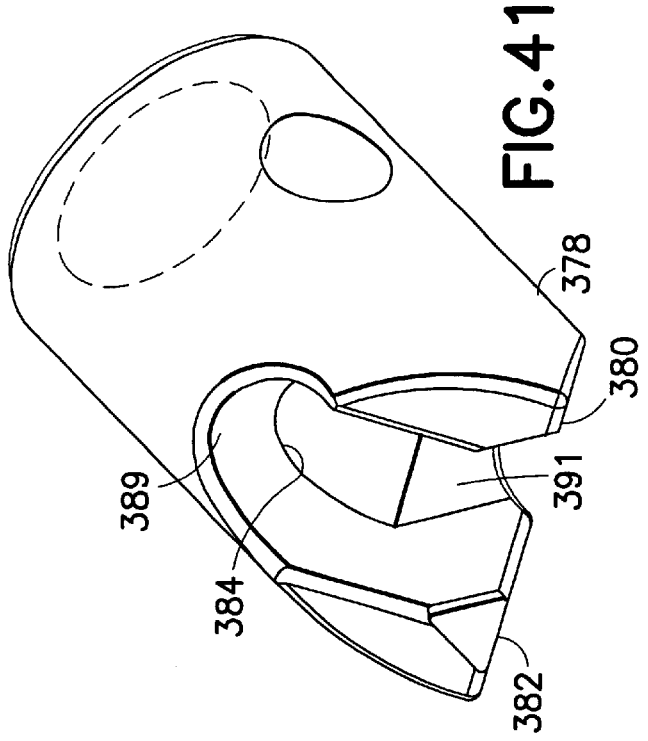
FIG. 41 is a perspective view of one of the positioning coupling element of FIG. 40.
Figure 42:
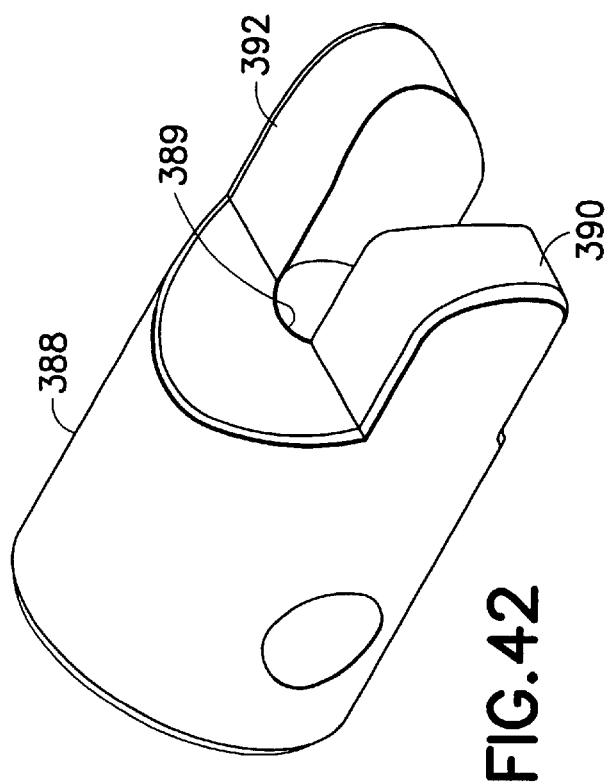
FIG. 42 is a perspective view of the drive coupling element of FIG. 40.
Figure 43:
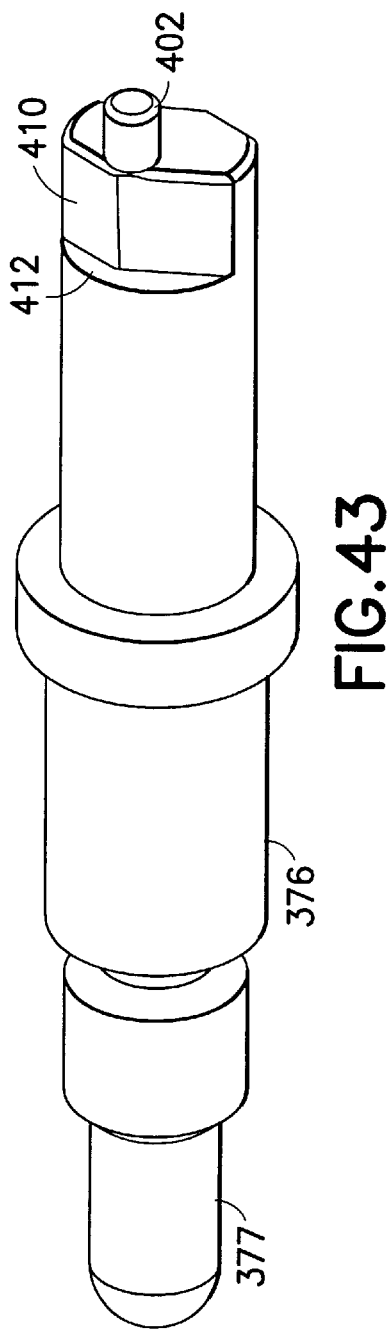
FIG. 43 is a perspective view of the cutter head drive shaft of the keratome of FIG. 30.

The automated drive unit 310 reciprocally translates the cutter head 330 of cutting instrument 314 on the suction ring 312. To this end, the cutting instrument 314 has a worm gear 340 extending from the tubular body 332 and the handle drive has a threaded shaft 342 (threads not shown) which is received in the worm gear 340. The threaded shaft 342 is rotatably mounted in a front plate 344 of the reciprocal handle drive 310. The other end of shaft 342 is mounted to rear plate 345 and has a gear 346, which meshes with a gear 348 of a drive motor 350, as best seen in FIGS. 37 and 38. When the motor 350 spins gears 348 and 346, the threaded shaft 342 translates the cutting instrument 314 into the suction ring and across the eye opening thereof, to incise the cornea. When the worm gear 340 engages bushing 334, the load on the motor 350 is increased suddenly and dramatically, causing an electrical spike which is used as a control signal to reverse the direction of the motor 350 and withdraw the cutting instrument 314. The electrical spike may also be used as a signal to stop operation of motor 352, which reciprocates the cutting blade in the cutter head 330 of the cutting instrument. When the motor 350 moves the cutting instrument 314 back into the reciprocal handle drive 310, a microswitch 354 is used to stop operation of the motor 350 when the cutting instrument is fully retracted. An electronics package 356 controls these operations, with external input via operating switches.

A coil spring 360 is mounted surrounding shaft 342 and provides a bias load between the threaded shaft 342 and the worm gear 340, which prevents any gear lash which might otherwise cause an unsmooth motion of the cutting instrument 314 in the suction ring 312.

With reference to FIGS. 31–36 and 39, the cutter head 330 has a cylindrical mounting shank 362 defining a bayonet mounting slot 364. The bayonet mounting slot cooperates with a pin 366 mounted to the tubular body 32 of the cutting instrument. More particularly, the bayonet mounting slot 364 defines an entry way 368, and a retention end 370 in which the pin 366 seats to lock the cutter head into the desired orientation on the tubular housing 332, and also provides for easy removal of the cutter head 330 for sterilization, or blade changes.

The cutting instrument includes a coupling 374, best seen in FIGS. 36 and 40–43, connecting the motor 352 and a drive shaft 376 extending through bearing block 372 into the cutter head 330 for oscillating a cutting blade, in the manner described above. The coupling 374 includes a first, positioning coupling member 378 having positioning ears 380 and 382, which are preferably pointed. The positioning coupling member 378 also includes a central opening 384 in which the drive shaft 376 is received with the end 377 thereof (FIG. 43) protruding through the coupling member 378. The coupling 374 further comprises the drive coupling member 388, characterized by rounded ears 390 and 392 which fit snugly in slots 389 and 391 of the positioning coupling member 378. Drive coupling member 388 also defines an axial opening 389, which receives the end 377 of drive shaft 376 when the coupling members are assembled together.

Therefore, when the cutter head 330 is removed from the remainder of the cutting instrument, the coupling members 378 and 388 separate, and when the cutter head is reattached, the drive ears 390 and 392 will either immediately settle into the slots 389, 391 or will engage against the pointed ears 380, 382 and be directed in to the slots 389, 391. As noted above, the drive shaft protrudes through the positioning coupling member 378 into opening 389 of the drive coupling member 388, for secure axial alignment of the coupling 374.

Figure 44:
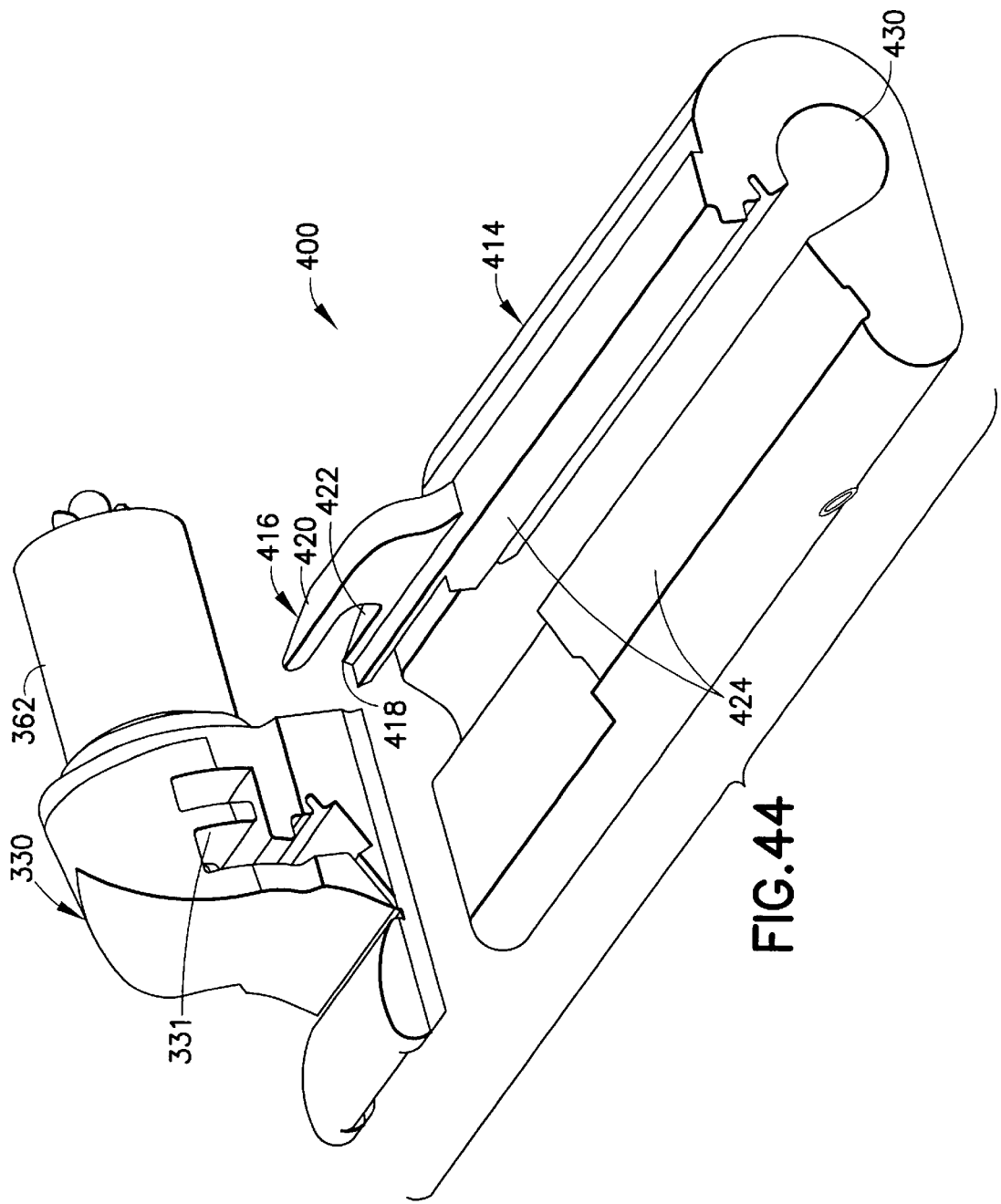
FIG. 44 is a perspective view of the cutter head of the keratome of FIG. 30, and one element of a blade insertion tool.
Figure 45:
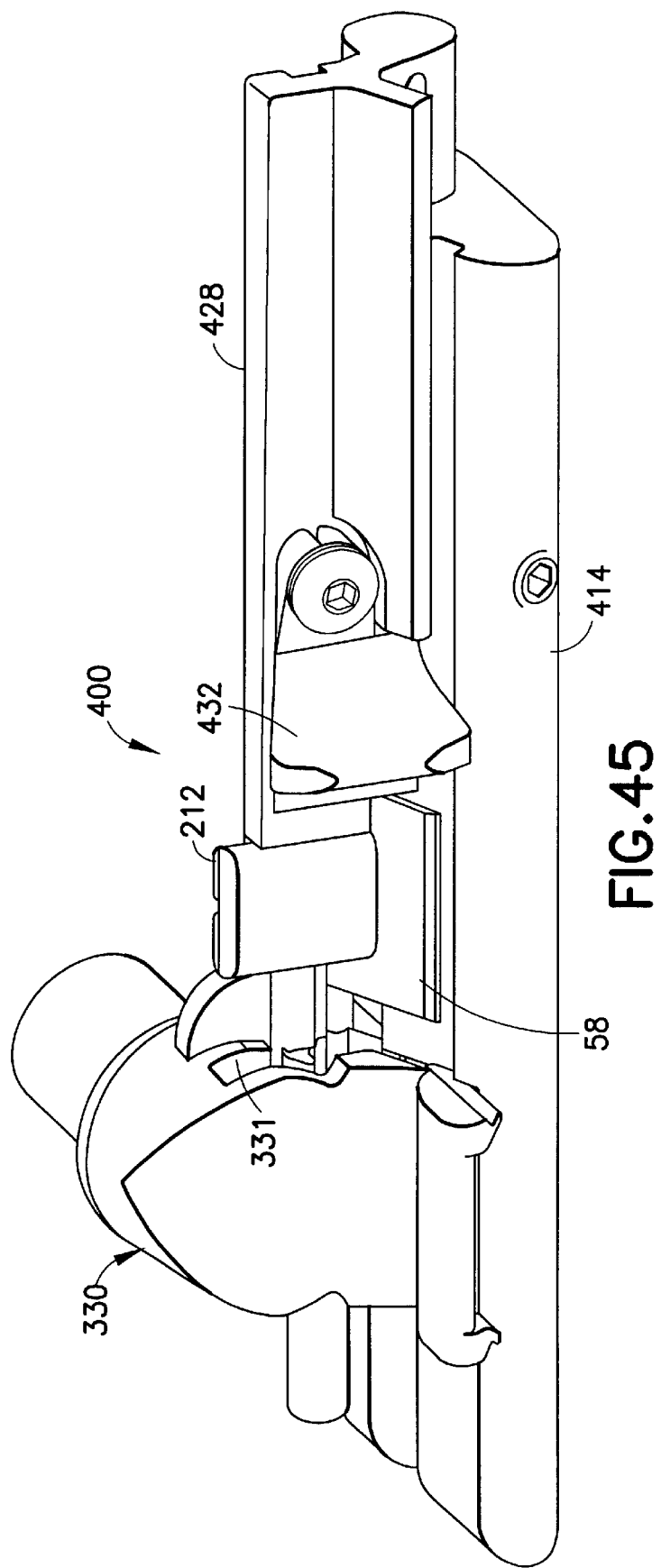
FIG. 45 is a perspective view of the cutter head and the element of the blade insertion tool of FIG. 44 shown inserted in the cutter head, and a second element of the blade insertion tool inserting a cutter blade assembly.
Figure 46:
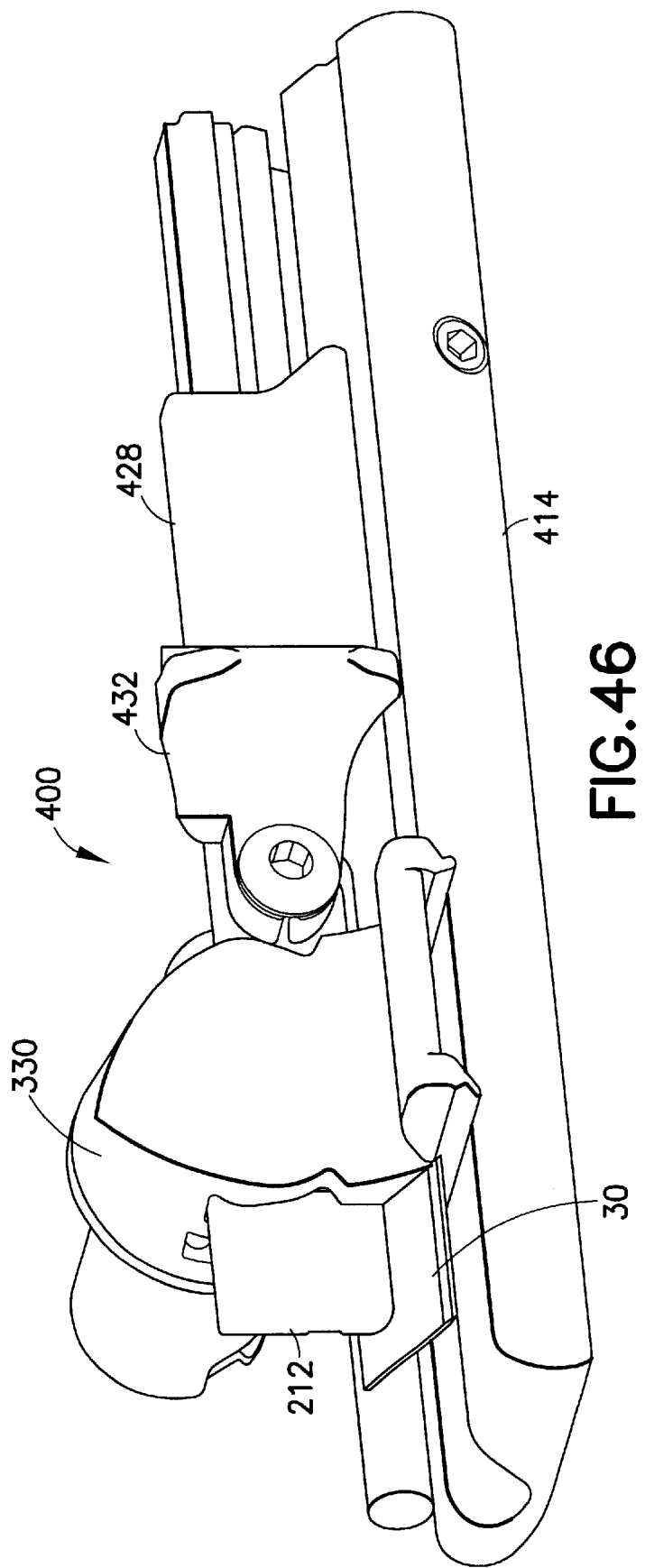
FIG. 46 is a perspective view of the cutter head, and first and second elements of the blade insertion tools shown removing a cutter blade from the cutter head.

The keratome 300 is also provided with an accessory blade insertion tool 400, shown in FIGS. 44–46, which operates with respect to the cutter head after its removal from the cutting instrument, by disengagement of the bayonet mount. The function of the blade insertion tool is to retract the drive shaft 376 in order to remove the drive pin 402 of the drive shaft from the blade cavity 331 defined in the cutter head 330, in order that a cutting blade assembly can be inserted without interference with the drive pin. To this end, the cutter head 330 is provided with an access slot 404 behind the blade holder cavity 331, the end 410 of the drive shaft is partially cut away with respect to the drive pin and further defines a shoulder 412, and the drive shaft is axially biased to position the drive pin in the blade cavity and provide for retraction from the blade holder cavity.

With reference to FIG. 44, the blade insertion tool 400 comprises a shaft retractor and blade holder 414, including a tip 416 having ramped back surfaces 418 and 420 for engaging the shoulder 412 of the drive shaft and pushing the drive shaft rearwardly. The tip 416 also defines a shaped slot 422 for receiving tip 410 of the drive shaft. The shaft retractor and blade holder 414 also defines a shaped blade assembly support surface, generally referred to at 424, for receiving and positioning a cutting blade 58 and blade holder 212 adjacent the cutter head 330, which is also supported on the shaft retractor and blade holder 414. FIG. 45 shows the shaft retractor with its tip 416 inserted in the cutter head 330, and the blade holder 212 is adjacent blade holder cavity 331 and blade 58 adjacent the blade slot.

With continued reference to FIG. 45, the blade insertion tool 400 further comprises an injector 428, which is received in groove 430 of the shaft retractor 414, and is slid therealong to push the blade 58 and blade holder 212 supported on the blade support surface 424 into the blade holder cavity 331 of the cutter head 330. The injector 428 has a pivotally mounted stop member 432 which, when oriented toward the cutter head 330 as shown in FIG. 45, abuts and stops against the cutter head 330 when the blade holder is inserted centrally in the blade holder cavity 331. Therefore, on withdrawal of the shaft retractor 414 and its tip 416, the drive pin 402 moves forward into the drive track of the blade. It may be necessary to rotate the drive shaft to seat the eccentric drive pin, but the drive track is accurately positioned to receive it.

When the stop member 432 is pivoted upwardly, as shown in FIG. 46, the injector 428 may be slid into the blade cavity 331, displacing the blade assembly therein and thus providing for removal of used blades.

It will be appreciated that in FIGS. 45 and 46, the cutter head 330 is shown disassociated from the other portions of the cutting instrument 314 and the automated drive unit 310, so that the drive shaft may be retracted. The bayonet mount of the cutter head and the coupling 374 facilitate easy removal and replacement of the cutter head and, together with the blade insertion tool, make it a simple matter to change blade assemblies.

The keratomes described above achieves very smooth incisions of the cornea in releasing a cornea segment, and does not damage or contaminate the cornea beyond the desired surgical incision.

Accordingly, keratomes have been described of which fulfill the objects of the invention herein. It will be appreciated by those skilled in the art that the keratomes described above are illustrative of the invention, but that various changes and adaptations can be made without departing from the spirit and scope of the invention, which is limited only by the following claims and structures which may fairly fall therebetween.

We claim:

1. A blade assembly for a keratome of the type including a cutter head defining a blade holder cavity, one of a guide bar or a guide slot, and a drive shaft opening to the blade cavity for receiving a drive shaft having an eccentric revolving drive pin extending into the blade cavity, the blade assembly comprising:
   A) a blade holder configured for reciprocal sliding movement in the blade holder cavity of the cutter head, the blade holder defining on a back surface thereof one of a guide slot or a guide bar for engagement with the one guide bar or guide slot defined by the cutter head, the blade holder further defining on the back surface thereof a drive track substantially perpendicular to the guide slot or guide bar defined by it for receiving the eccentric revolving drive pin; and
   B) a blade mounted to the blade holder and extending therefrom to a blade edge substantially parallel to the guide slot or guide bar defined by the blade holder.

2. A blade assembly as defined in claim 1 wherein the cutter head defines a guide bar and the back surface of the blade holder defines the guide slot for engagement with a guide bar of the cutter head.

3. A blade assembly as defined in claim 2 wherein the guide slot has a shape complementary with the guide bar for sliding engagement therewith.

4. A blade assembly as defined in claim 2 wherein the blade holder is fabricated of a polymer.

5. A blade assembly as defined in claim 4 wherein the polymer is nylon.

6. A blade assembly as defined in claim 2 wherein the blade holder has a bottom to which the blade is mounted.

7. A blade assembly as defined in claim 6 wherein the bottom defines a mounting stud and the blade defines an opening in which the mounting stud is received to mount the blade.

8. A blade assembly as defined in claim 2 wherein the guide slot is disposed between the drive track and the bottom of the blade holder.

9. A blade assembly as defined in claim 2 wherein the blade holder has a top that slidingly engages against a top of the blade holder cavity and the distance from the guide slot to the top of the blade holder is larger than the distance from the guide bar of the cutter head to the top of the blade holder cavity.

10. A blade assembly as defined in claim 9 wherein the distance from the guide slot to the top of the blade holder is about 0.0005–0.0010 inches larger than the distance from the guide bar of the cutter head to the top of the blade holder cavity.

11. A blade assembly for a keratome of the type including a cutter head defining a blade holder cavity having a guide bar and a drive shaft opening to the blade cavity for receiving a drive shaft having an eccentric revolving drive pin extending into the blade cavity, the blade assembly comprising:
   A) a blade holder configured for reciprocal sliding movement in the blade holder cavity of the cutter head, the blade holder having a back surface defining a rounded guide slot for engagement with the guide bar defined by the cutter head, the blade holder further defining a drive track substantially perpendicular to the guide slot defined by it for receiving the eccentric revolving drive pin; and
   B) a blade mounted to the blade holder and extending therefrom to a blade edge substantially parallel to the guide slot defined by the blade holder.

12. A blade assembly for a keratome of the type including a cutter head defining a blade holder cavity having a guide bar and a drive shaft opening to the blade cavity for receiving a drive shaft having an eccentric revolving drive pin extending into the blade cavity, the blade assembly comprising:
   A) a blade holder configured for reciprocal sliding movement in the blade holder cavity of the cutter head, the blade holder having a back surface defining a guide slot for engagement with the guide bar defined by the cutter head, the blade holder further defining a drive track defined on the back surface of the blade holder substantially perpendicular to the guide slot defined by it for receiving the eccentric revolving drive pin, wherein the drive track intersects the guide slot; and
   B) the blade holder having a bottom and a blade mounted to the bottom of the blade holder and extending therefrom to a blade edge substantially parallel to the guide slot defined by the blade holder.

13. A blade assembly for a keratome of the type including a cutter head defining a blade holder cavity and a rectangular guide bar extending into the blade cavity, and a drive shaft opening to the blade cavity for receiving a drive shaft having an eccentric revolving drive pin extending into the blade cavity, the blade assembly comprising:

A) a blade holder configured for reciprocal sliding movement in the blade holder cavity of the cutter head, the blade holder defining a rectangular guide slot for complementary engagement with the guide bar defined by the cutter head, the blade holder further defining a drive track substantially perpendicular to the guide slot, for receiving the eccentric revolving drive pin; and B) a blade mounted to the blade holder and extending therefrom to a blade edge substantially parallel to the guide slot or guide bar defined by the blade holder.

* * * * *